United States Patent
Lanzani et al.

(10) Patent No.: US 11,401,250 B2
(45) Date of Patent: Aug. 2, 2022

(54) PHOTOCHROMIC COMPOUNDS FOR USE IN THE TREATMENT OF EYE DISORDERS

(71) Applicants: FONDAZIONE ISTITUTO ITALIANO DI TECNOLOGIA, Genoa (IT); POLITECNICO DI MILANO, Milan (IT)

(72) Inventors: Guglielmo Lanzani, Milan (IT); Giuseppe Maria Paterno', Enna (IT); Francesco Lodola, Pavia (IT); Chiara Bertarelli, Lecco (IT); Fabio Benfenati, Genoa (IT); Mattia Lorenzo DiFrancesco, Milan (IT); Elisabetta Colombo, Genoa (IT); Josè Fernando Maya-Vetencourt, Pisa (IT); Letizia Colella, Vicenza (IT)

(73) Assignees: FONDAZIONE ISTITUTO ITALIANO DI TECNOLOGIA, Genoa (IT); POLITECNICO DI MILANO, Milan (IT)

( * ) Notice: Subject to any disclaimer, the term of this patent is extended or adjusted under 35 U.S.C. 154(b) by 0 days.

(21) Appl. No.: 16/972,336

(22) PCT Filed: May 31, 2019

(86) PCT No.: PCT/IB2019/054530
§ 371 (c)(1),
(2) Date: Dec. 4, 2020

(87) PCT Pub. No.: WO2019/234567
PCT Pub. Date: Dec. 12, 2019

(65) Prior Publication Data
US 2021/0238156 A1 Aug. 5, 2021

(30) Foreign Application Priority Data
Jun. 4, 2018 (IT) .................... 102018000005987

(51) Int. Cl.
*C07D 295/135* (2006.01)
*A61P 27/02* (2006.01)

(52) U.S. Cl.
CPC .......... *C07D 295/135* (2013.01); *A61P 27/02* (2018.01)

(58) Field of Classification Search
CPC ................................. C07D 295/135
See application file for complete search history.

(56) References Cited

U.S. PATENT DOCUMENTS 3,538,074 A 11/1970 Hegar
3,666,746 A 5/1972 Stanley et al.

FOREIGN PATENT DOCUMENTS

JP 2003-232919 A 8/2003
WO 2009/051670 A2 4/2009

OTHER PUBLICATIONS

Huang, et al. Document No. 166:369028, retrieved from STN; Dec. 25, 2012.*
Damerau, W. Document No. 67:19518, retrieved from STN; (1966).*
Hayashi, et al. Document No. 69:42567, retrieved from STN; (1967).*
Hoshowski, M. Document No. 120:307076, retrieved from STN; Apr. 6, 1994.*
Hyde, et al. Document No. 152:282077, retrieved from STN; Feb. 18, 2010.*
Lowery, et al. Document No. 89:157137, retrieved from STN; (1978).*
Mukherjee, et al. Document No. 163:579658, retrieved from STN; Oct. 15, 2015.*
Murtaza, et al. Document No. 164:302236, retrieved from STN; (2015).*
Nachbaur, et al. Document No. 158:253787, retrieved from STN; Feb. 14, 2013.*
Wanker, et al. Document No. 166:322483, retreived from STN; Mar. 10, 2015.*
Yin, et al. Document No. 169:20886, retrieved from STN; May 15, 2018.*
Etzback, et al. Document No. 120:246105, retrieved from STN; May 14, 1994.*
International Search Report and Written Opinion of the International Searching Authority for International Patent Application No. PCT/IB2019/054530 dated Aug. 2, 2019, 14 pages.
Diguet, A. et al., "UV-Induced Bursting of Cell-Sized Multicomponent Lipid Vesicles in a Photosensitive Surfactant Solution", Journal of the American Chemical Society, 34(10): 4898-4904 (Feb. 2012).
Hashimoto, Y., "Structural development of biological response modifiers based on thalidomide", Bioorganic & Medicinal Chemistry, 10(3): 461-479 (Jan. 2002).
Kaspar, M. et al., "Thermal Properties of Liquid-Crystalline Diols and Corresponding Bis-Urethanes with Mesogenic Groups of Various Structures in Side Chains", Molecular Crystals and Liquid Crystals, 392(1): 17-30 (Jan. 2003).
Mourot, A. et al., "Themed Section: Recent Advances in Targeting Ion Channels to Treat Chronic Pain, Research Paper: Understanding and improving photo-control of ion channels in nociceptors with azobenzene photo-switches", British Journal of Pharmacology, 175: 2296-2311 (Jul. 2017).
Peddie, V. et al., "Synthesis and Solution Aggregation Studies of a Suite of Mixed Neutral and Zwitterionic Chromophores for Second-Order nonlinear Optics", Journal of Organic Chemistry, 79(21): 10153-10169 (Oct. 2014).

(Continued)

*Primary Examiner* — Shawquia Jackson
(74) *Attorney, Agent, or Firm* — Merchant & Gould P.C.

(57) ABSTRACT

Compounds have a formula (1) wherein Y and Z are independently O, N, P; R, $R^1$, $R^2$, $R^3$, where present, are independently H. Optionally substituted $C_1$-$C_{12}$ alkyl, O, or R and $R^1$ and/or $R^2$ and $R^3$ form, together with the atom Y and/or Z to which they are attached, a 3-14 membered ring. The compounds optionally contain one or more additional heteroatoms selected from O, N, and S, optionally substituted. Compositions include such compounds and the medical uses utilize such compounds.

6 Claims, 18 Drawing Sheets

(56) References Cited

OTHER PUBLICATIONS

Penchev, A. et al., "Properties of Azo Dyes Derived from 2-(N-Substituted Alkyl-N-Arylamino) Ethyltrimethyl-Ammonium Salts. Part I: Phenylamino Derivatives", Dyes and Pigments, 18(3): 227-235 (Jan. 1992).

Tirelli, N. et al., "Structure-Activity Relationship of New Organic NLO Materials Based on Push-Pull Azodyes. 1. Synthesis and Molecular Properties of the Dyes", Journal Fuer Praktische Chemie, 340(2): 122-128 (Jan. 1998).

Xiao, R. et al., "A Photo-responsive Catalytic Vesicle with GPx Activity", Chinese Journal of Chemistry, 32(1): 37-43 (Dec. 2013).

Zhang, Q. et al., Liquid Crystallinity and Other Properties in Complexes of Cationic Azo-Containing Surfactomesogens with Poly(styrenesulfonate), Macromolecules, 42(13): 4775-4786 (Jul. 2009).

Zhou, J. et al., "Synthesis, thermal stability and photoresponsive behaviours of azobenzene-tethered polyhedral oligomeric silsesquioxanes", New Journal of Chemistry, 35(12): 2781-2792 (Jan. 2011).

Bandara, H. et al., "Photoisomerization in different classes of azobenzene", Chem. Soc. Rev., 41: 1809-1825 (2012).

Bianco, A. et al., "Control of optical properties through photochromism: a promising approach to photonics", Laser Photonics Rev., 5(6): 711-736 (2011).

Fortin, D. et al., "Photochemical control of endogenous ion channels and cellular excitability", Nature Methods, 5(4): 331-338 (Apr. 2008).

Gorostiza, P. et al., "Optical switches and triggers for the manipulation of ion channels and pores", Molecular BioSystems, 3(10): 686-704 (Oct. 2007).

Hamryszak, L. et al., "New thermotropic symmetrical and unsymmetrical azomethine with azobenzene unit and fluorinated alkyl chain: Synthesis and characterization", Journal of Molecular Liquids, 165: 12-20 (2012).

Polosukhina, A. et al., "Photochemical Restoration of Visual Responses in Blind Mice", Neuron, 75: 271-282 (Jul. 2012).

Tochitsky, I. et al., "Restoring Visual Function to Blind Mice with a Photoswitch that Exploits Electrophysiological Remodeling of Retinal Ganglion Cells", Neuon, 81: 800-813 (Feb. 2014).

Tochitsky, I. et al., "Restoring visual function to the blind retina with a potent, safe and long-lasting photoswitch", Nature, Scientific Reports, 7:45487, 1-8 (2017).

\* cited by examiner

Az/2C₆Am ic macular degenera-
PHOTOCHROMIC COMPOUNDS FOR USE IN THE TREATMENT OF EYE DISORDERS This application is a National Stage Application of PCT/IB2019/054530, filed 31 May 2019, which claims benefit of Patent Application Serial No. 102018000005987, filed 4 Jun. 2018 in Italy and which applications are incorporated herein by reference. To the extent appropriate, a claim of priority is made to each of the above-disclosed applications.

The present patent application finds application in the medical field and, in particular, for the treatment of degenerative retinal diseases.

BACKGROUND ART

Retinal dystrophies, hereditary or due to age, such as retinitis pigmentosa (RP) and age-related macular degeneration (AMD), are among the prevalent causes of blindness. These diseases involve the degeneration of photoreceptors which causes a progressive and severe loss of vision.

RP is caused by dominant, recessive or X-linked mutations, involving genes involved in phototransduction. Mutations of these genes impair rod survival. Consequently, in RP the scotopic vision is precociously affected. In the following phases, the cones are involved up to causing total blindness.

AMD consists of a selective degeneration of foveal cones and affects up to 20% of the population over 75 years of age. In AMD, impairment of foveal photoreceptors results in high resolution vision loss in the central area of the visual field.

Despite numerous efforts, a recognized pharmacological treatment to prevent photoreceptor degeneration has not yet been identified. Given the relative conservation of the internal retina, attempts have been made to restore the vision through the photostimulation of the latter.

Bianco A et al. (*Control of optical properties through photochromism: a promising approach to photonics*. Laser Photonics Rev 2011; 1-26) describe photochromic molecules for photoactivation of the internal retina. Typically, the photoisomerizable portion of the molecule is an azobenzene which exposes an active group changing between a dark and light state, with isomerization from trans (E) to cis (Z).

The properties related to the isomerization of the azobenzene derivatives have been extensively studied, for example for applications related to ion channels, voltage or ligand-dependent. See Gorostiza P and Isacoff E (*Optical switches and triggers for the manipulation of ion channels and pores*. Mol Biosyst 2007; 3, 686-704).

Photoswitchable affinity labels (PAL) have also been described to induce light-dependent conformational changes in target proteins in the absence of engineering and expression of exogenous genes (Fortin DL et al. *Photochemical control of endogenous ion channels and cellular excitability*. Nat Methods 2008; 5, 331-338). Among these, Polosukhina A et al. (*Photochemical restoration of visual responses in blind mice*. Neuron 2012; 75, 271-282) described compounds which covalently bind to one end of azobenzene a quaternary ammonium group (QA) which binds and blocks the $K^+$ channels and, at the other end, a polar group, such as acrylamide, which interacts with the channel structure. Said compounds were able to recover visual activity in genetically blind mice. The effect found, after intravitreal administration of the compound, was short-lived and required UV illumination to promote isomerization from E to Z. The drawback is related to the need for excitation in the UV region, which is harmful to the tissue and hardly reaches the retina. The need to have new azobenzenic photoswitches substituted with quaternary ammonium, which can be activated by visible light and show a longer half-life, led to describe the DENAQ and BENAQ (Tochitsky I et al. *Restoring visual function to blind mice with a photoswitch that exploits electrophysiological remodeling of retinal ganglion cells*. Neuron 2014; 81, 800-813. Tochitsky I et al. *Restoring visual function to the blind retina with a potent, safe and long-lasting photoswitch*. Sci Rep 2017; 7, 45487).

Despite the numerous efforts made so far in the field of optical stimulation of excitable cells, there is still a strong need for new photochromic compounds which are at the same time biocompatible, activatable with visible light, with greater half-life and which do not interfere with the natural physiological activity of membrane channels.

SUMMARY

Photochromic compounds are described herein which are located inside the cell membrane at the lipid rafts.

A further object of the present invention relates to said compounds for use in the treatment of degenerative diseases of the retina.

OBJECT OF THE INVENTION

Another object of the present invention is a pharmaceutical composition comprising at least one of the compounds described.

In a further object, it is described the medical use of the compounds of the invention.

The process for the preparation of the compounds described represents a still further object of the invention.

DETAILED DESCRIPTION OF THE INVENTION

Figure 1:
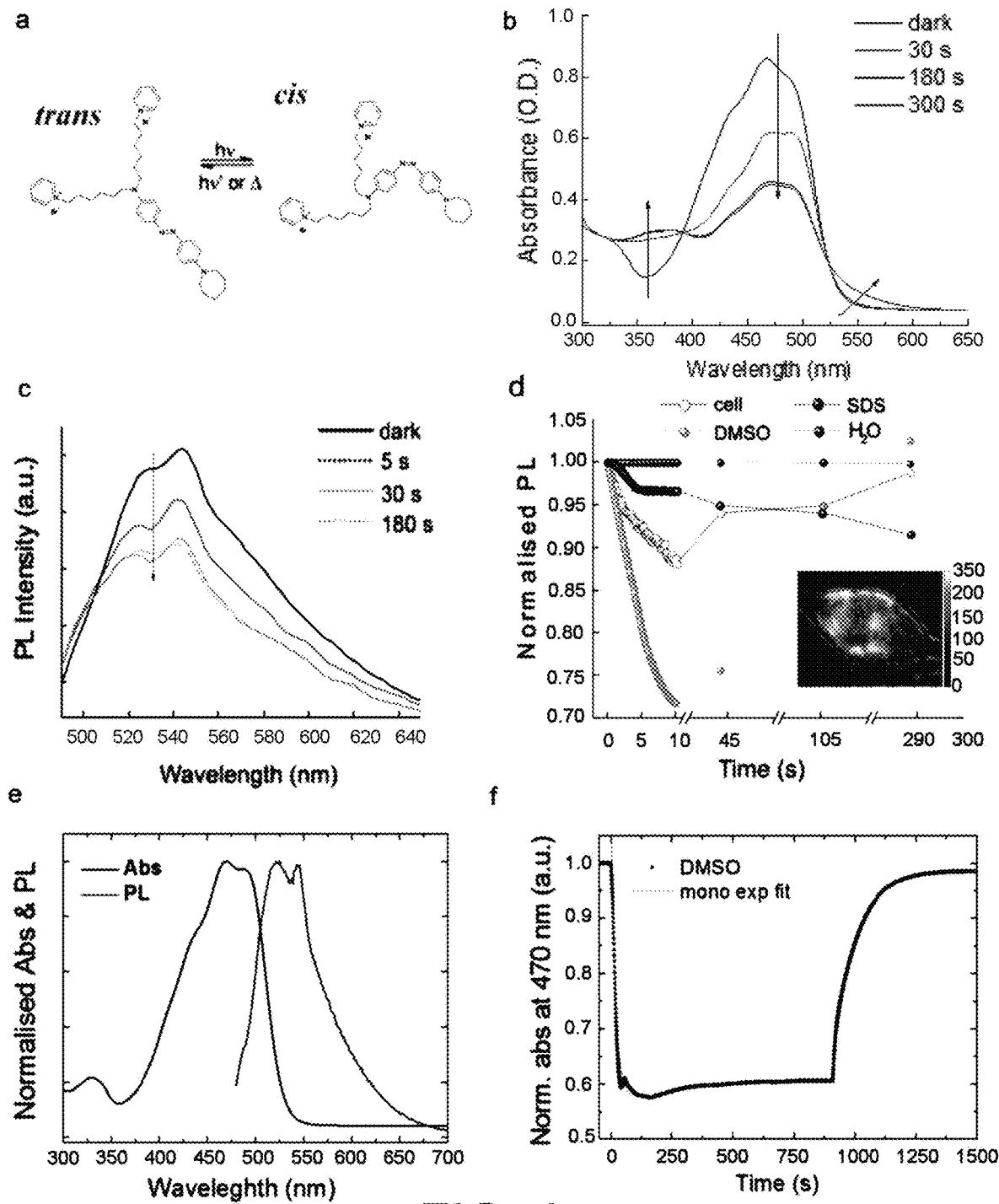
FIG. 1: (a) scheme of the isomerization process of a compound according to the present invention. Absorption (b) and emission (c) spectra of the compound Ziapin 2 25 µM in DMSO. (d) photoswitching dynamics of Ziapin 2 in water, DMSO and in $HEK_{293}$ cells. (e, f) absorption and photoluminescence of Ziapin 1 25 µM in DMSO (e) and evolution of the absorption peak at 470 nm by illuminating with a diode at 450 nm (f).

Unless otherwise defined, all the technical and scientific terms used herein have the same meaning as commonly understood by a person skilled in the art. In the event that there is a plurality of definitions for the terms, those in this section prevail.

In this application, the use of the singular includes the plural, unless specifically indicated otherwise. It must be indicated that, as used in the description and in the appended claims, the singular forms "a", "an" and "the" include plural references, unless the context clearly dictates otherwise.

The term "optional" or "optionally" means that the event or circumstance described below may or may not occur and that the description includes examples where the aforementioned event or circumstance occurs and examples in which they do not occur. For example, "optionally substituted alkyl" means "alkyl" or "substituted alkyl"; moreover, an optionally substituted group may be unsubstituted (for example, —CH$_2$CH$_3$), completely substituted (for example, —CF$_2$CF$_3$), monosubstituted (for example, —CH$_2$CH$_2$F) or substituted at a level anywhere in the medium completely substituted and monosubstituted (for example, —CH$_2$CHF$_2$, —CH$_2$CF$_3$, —CF$_2$CH$_3$, —CFHCHF$_2$, etc.).

As used herein, C1-Cx includes C1-C2, C1-C3 . . . C1-Cx. By way of example only, "C1-C4" indicates that there are one to four carbon atoms in the functional group, i.e. groups containing 1 carbon atom, 2 carbon atoms, 3 carbon atoms or 4 carbon atoms, as well as the C1-C2 and C1-C3 ranges. Therefore, by way of example only, "C1-C4 alkyl" indicates that there are one to four carbon atoms in the alkyl group, that is, the alkyl group is selected from methyl, ethyl, propyl, isopropyl, n-butyl, isobutyl, sec-butyl and t-butyl. Whenever it appears herein, a numerical range, such as "1 to 10", refers to each integer in the given range; for example, "1 to 10 carbon atoms" means that the group can have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. The terms "ring" and "terminus ring" as used herein, alone or in combination, refer to any covalently closed structure, including heteroaromatic and polycyclic, alicyclic, heterocyclic, aromatic ring systems, fused or not fused, as described herein.

The rings may optionally be substituted.

The rings may be part of a fused ring system.

The term "terminus" is meant to indicate the number of backbone atoms that make up the ring.

The term "fused" as used herein, alone or in combination, refers to cyclical structures in which two or more rings share one or more bonds.

By the term "substituted", it is meant substituted with one or more substituents independently selected from halogen, alkyl, hydroxy, alkoxy.

In the present invention, the term "3-14-membered heterocycle" means a cyclic group derived from a hydrocarbon by removing a hydrogen atom. As an example, the term includes monocyclic heterocycles with 3-8 members and fused heterocycles with 6-14 members.

The term "monocyclic heterocycle with 3-8 members" means saturated monocyclic heterocycles with 3-8 members and partially saturated monocyclic heterocycles. The term "saturated monocyclic heterocycle with 3-8 members" means that the monocyclic ring is a completely saturated ring.

The term "partially saturated monocyclic heterocycle with 3-8 members" means that the monocyclic ring is a partially saturated ring.

According to a first object of the invention, compounds of formula (1) are described

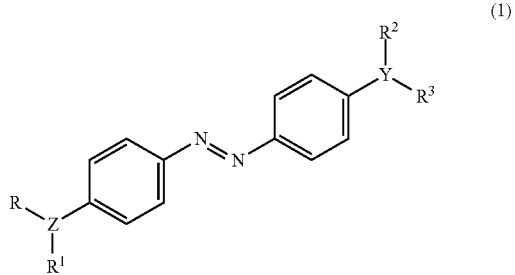

(1)

where Y and Z are independently O, N, P;

R, $R^1$, $R^2$, $R^3$, where present, are independently H, optionally substituted $C_1$-$C_{12}$ alkyl, preferably optionally substituted $C_1$-$C_6$ alkyl, O, or R and $R^1$ and/or $R^2$ and $R^3$ form, together with the atom Y and/or Z to which they are attached, a 3-14 membered ring, optionally containing one or more additional heteroatoms selected from O, N, and S, optionally substituted.

Preferably, said $C_1$-$C_6$ alkyl is an optionally substituted linear chain or optionally substituted branched chain saturated hydrocarbon.

Even more preferably, said $C_1$-$C_6$ alkyl is substituted at the C terminal with a positively charged group, preferably with a tertiary amino group or with an aromatic amine.

In a preferred aspect of the invention, R, $R^1$, $R^2$ and/or $R^3$ are independently

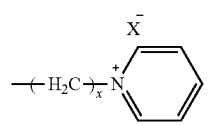

wherein X=Br, I and x is comprised between 2 and 12; or R, $R^1$, $R^2$ and/or $R^3$ are independently

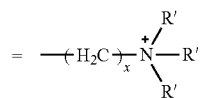

wherein X=Br, I, x is comprised between 2 and 12 and R' is $C_1$-$C_4$ alkyl, preferably R'=$CH_3$, $CH_2CH_3$.

According to a preferred aspect of the present invention, in the described compounds of formula (1) Z is N and said R and $R^1$ are independently H and/or

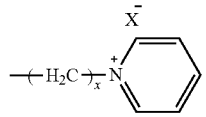

and X=Br or I and x is comprised between 2 and 12.

According to another preferred aspect of the present invention, in the described compounds of formula (1) Y is N and said R2 and R3 are both

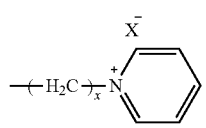

and X=Br or I and x is comprised between 2 and 12.

In a particular aspect of the invention, when Y and/or Z are O, said R or $R^1$ and/or said $R^2$ or $R^3$ are optionally absent.

According to a preferred aspect, said groups $ZRR_1$ and/or $YR_2R_3$ are $NO_2$.

In a further preferred aspect, said groups $ZRR_1$ and/or $YR_2R_3$ are —$OCH_3$.

Said ring is a saturated, unsaturated or aromatic ring and, when substituted, it is substituted with one or more substituents independently selected from methyl, ethyl, propyl, isopropyl, tert-butyl, cyclopropyl, cyclobutyl, —$CF_3$, —OH, —$OCH_3$, —$OC_2H_5$, —SH, —$SCH_3$, —$SCH_2CH_3$, —$CH_2OH$, —$C(CH_3)_2OH$, —Cl, —F, —CN, —COOH, —COORS, —$CONH_2$, —$CONHR^5$ or —$SO_2NH_2$; wherein R5 is H or $C_1$-$C_3$ alkyl.

In a preferred aspect, said ring comprises carbon atoms, except the atom Y or Z.

In an even more preferred aspect, said ring is an azepane.

For the purposes of the present invention, the compounds of Table 1 are particularly preferred:

TABLE 1

TABLE 1-continued
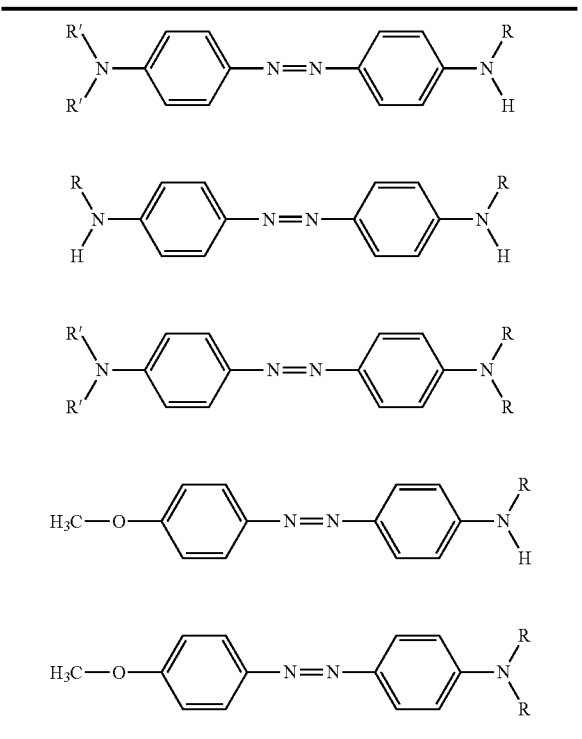
TABLE 1-continued
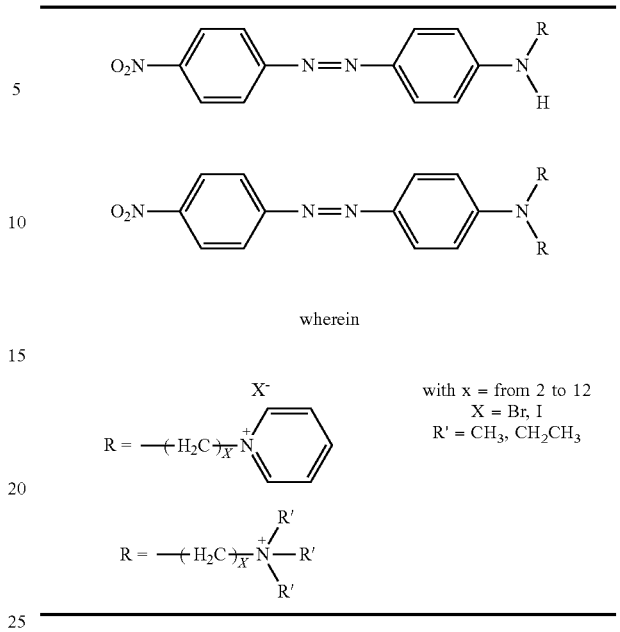
wherein
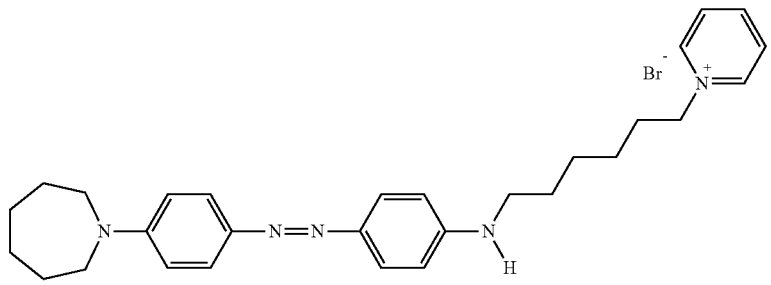
with x = from 2 to 12
X = Br, I
R' = CH$_3$, CH$_2$CH$_3$
with X=Br or I, x is comprised between 2 and 12, R'=—CH$_3$, —CH$_2$CH$_3$.
According to a particularly preferred aspect of the present invention, the following compounds are described:
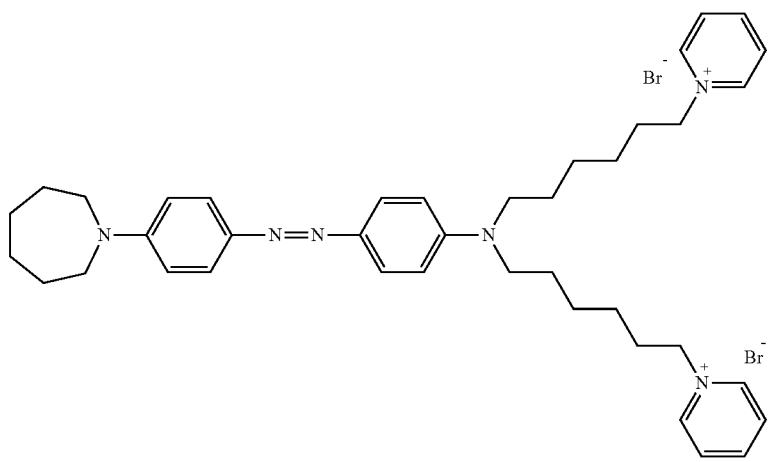
Ziapin 1
Ziapin 2

-continued
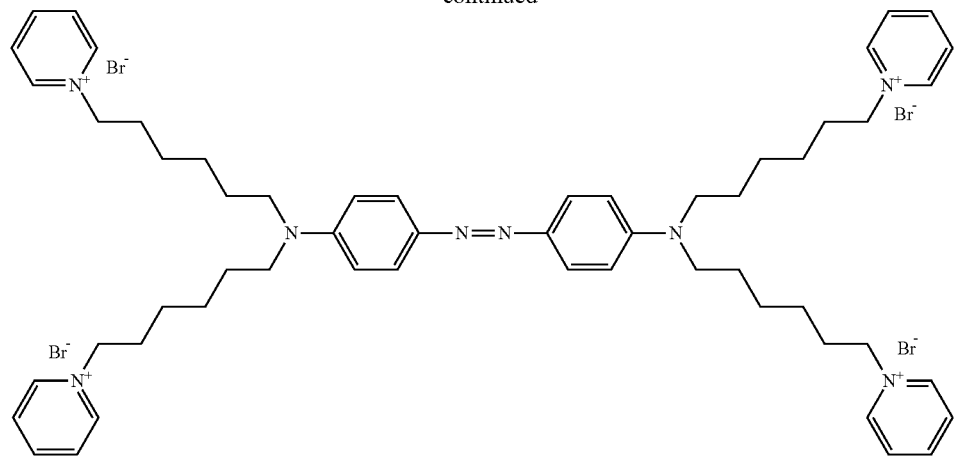
2C$_6$Py/2C$_6$Py
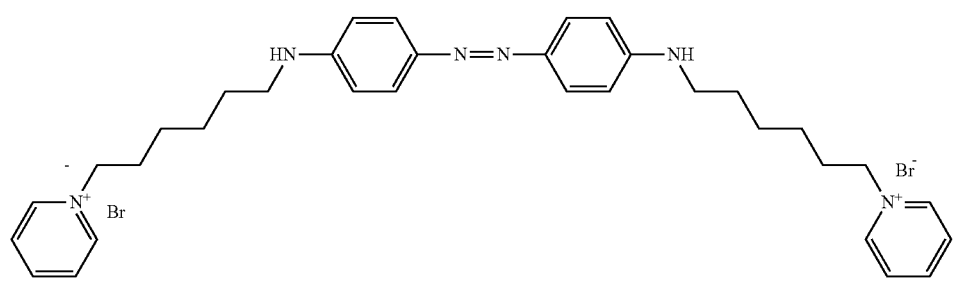
1C$_6$Py/1C$_6$Py
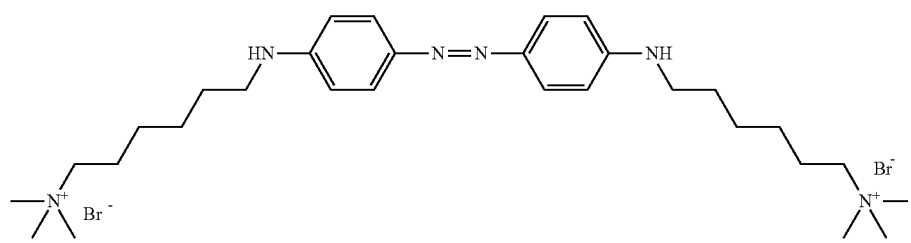
1C$_6$Am/1C$_6$Am
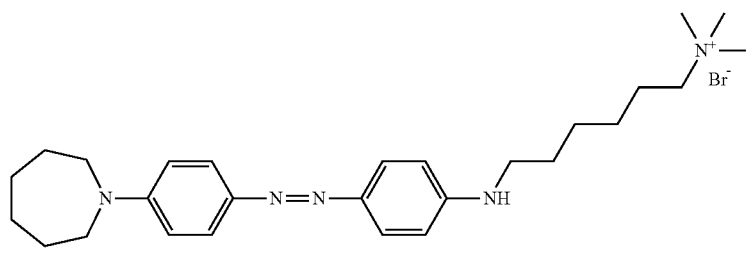
Az/1C$_6$Am -continued
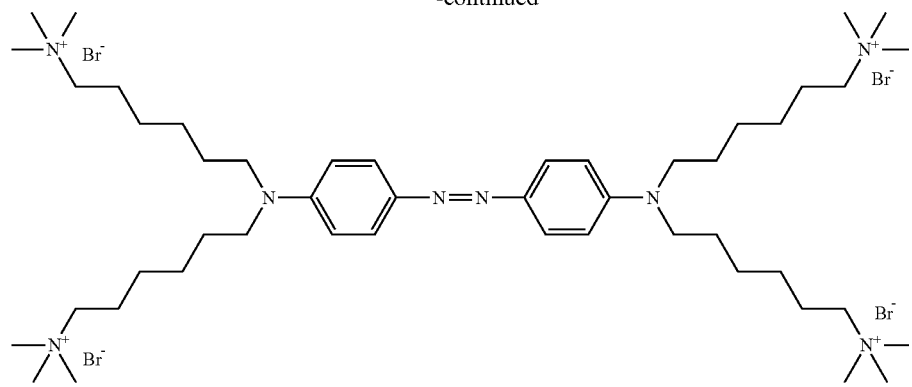
2C$_6$Am/2C$_6$Am
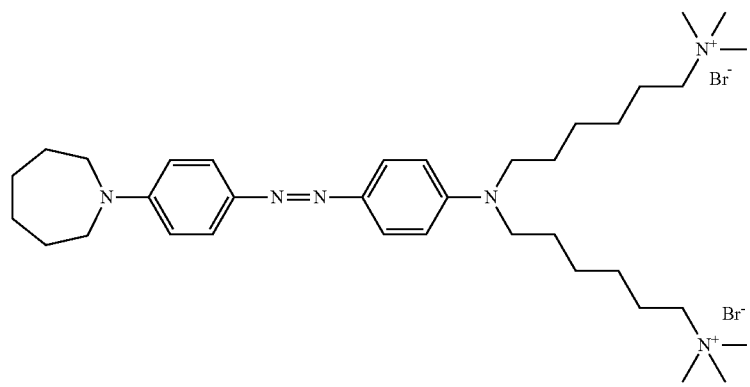
Az/2C$_6$Am
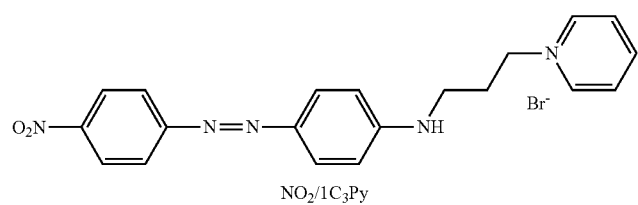
NO$_2$/1C$_3$Py
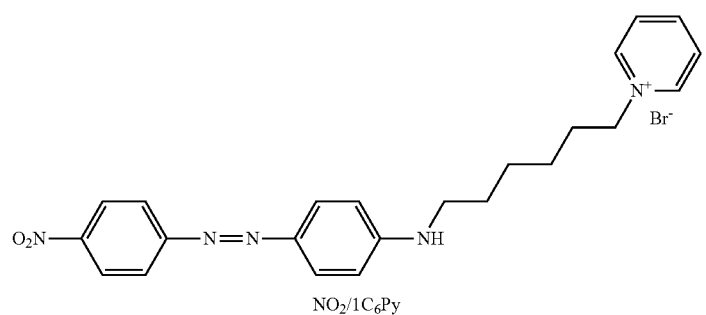
NO$_2$/1C$_6$Py -continued

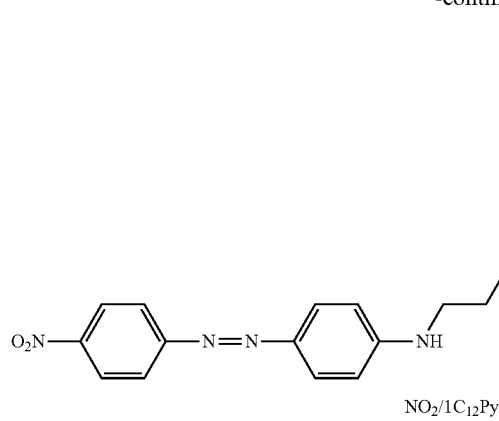

NO$_2$/1C$_{12}$Py

The compounds described herein for medical use further form the object of the present invention.

In a preferred aspect, said medical use is in the treatment of eye diseases.

Even more preferably, said medical use is in the treatment of eye diseases, which are retinal dystrophies, for example retinitis pigmentosa and age-related macular degeneration.

In a further aspect, a composition is described which comprises at least one of the compounds according to the present invention and, optionally, one or more further pharmaceutically acceptable active ingredients and/or excipients.

The pharmaceutical compositions for use according to the present invention may be formulated in a conventional manner using one or more pharmaceutically acceptable excipients including carriers, diluents or liposomes which facilitate the processing of the active compounds in preparations, which can be used physiologically for the microinjectable preparation.

In a preferred aspect, the compounds of the invention are provided as pharmaceutical compositions in the form of liquid compositions.

The pharmaceutical composition may contain at least one of said compounds dispersed in a suitable liquid excipient.

Suitable liquid excipients are known in the art; see, for example, Remington's Pharmaceutical Sciences.

In a particularly preferred embodiment, said formulation is by intravitreal or subretinal microinjection.

A further object of the present invention is a method for the treatment of degenerative diseases of photoreceptors which comprises the administration, preferably by intravitreal or subretinal microinjection at the macular region, of a suitable amount of at least one of the compounds according to the present invention to a patient in need thereof.

The administration may be repeated following the possible attenuation of the photosensitivity.

The term "microinjection" refers to the administration of the preparation using a microsyringe so as to slowly and regularly inject volumes in the order of microliters locally.

The compounds or compositions according to the present invention are administered at the subretinal level by microinjection through the sclera or through the vitreous chamber.

According to a preferred aspect, the compounds or the composition according to the present invention are administered/applied/injected by microinjection into the subretinal space.

Preferably, said compounds or composition are administered by one of the following methods.

(i) Making an incision in the conjunctiva of the eye to be treated, preferably with scissors 1.5 mm from the limbus at about 2 o'clock in the upper quadrants; and/or (ii) Incising the sclera and the choroid (about 0.6 mm), preferably 1 mm from the limbus; and/or (iii) Separating the retina from the retinal pigment epithelium by injecting a small amount of viscoelastic material into the subretinal space, such as high molecular weight hyaluronic acid sodium salt (e.g., IAL-F, Fidia Farmaceutici S.p.A., Italy); and/or (iv) Injecting one or more of the compounds or the composition according to the present invention, preferably through the sclera in the subretinal space;

(vi) Coagulating the scleral incision by diathermy and repositioning the conjunctiva on the scleral wound.

In a preferred aspect thereof, one or more of the compounds or the composition according to the present invention are administered by microinjection in the subretinal region preferentially at the macula after penetration through the sclera and the choroid.

In a preferred aspect thereof, one or more of the compounds or the composition according to the present invention are administered by microinjection in the subretinal region.

According to another preferred aspect, the injection is performed by opening the conjunctiva, incising the sclera and the choroid, separating the sclera and the pigmented epithelium of the retina, injecting a viscoelastic material into the retina and finally injecting one or more of the compounds or the composition according to the present invention into the subretinal region.

According to a further preferred aspect, one or more of the compounds or the composition according to the present invention are injected tangentially to the sclera, in order to prevent any damage to the retina and the choroid. The tangential sub-retinal flow originating by injecting with the needle in this position is very effective in promoting a complete retinal detachment and a consequent uniform distribution of the compound.

Said composition is preferably an injectable ophthalmic pharmaceutical composition.

The ophthalmic composition of the present invention is characterized by a generally acceptable pH for ophthalmic applications and, preferably, comprised between 7.0 and 7.5.

Furthermore, the composition is characterized by an osmotic pressure generally acceptable for ophthalmic applications and, preferably, comprised between 290 and 300 mOsm/L.

EXAMPLES

Synthesis Strategy

Figure 10:
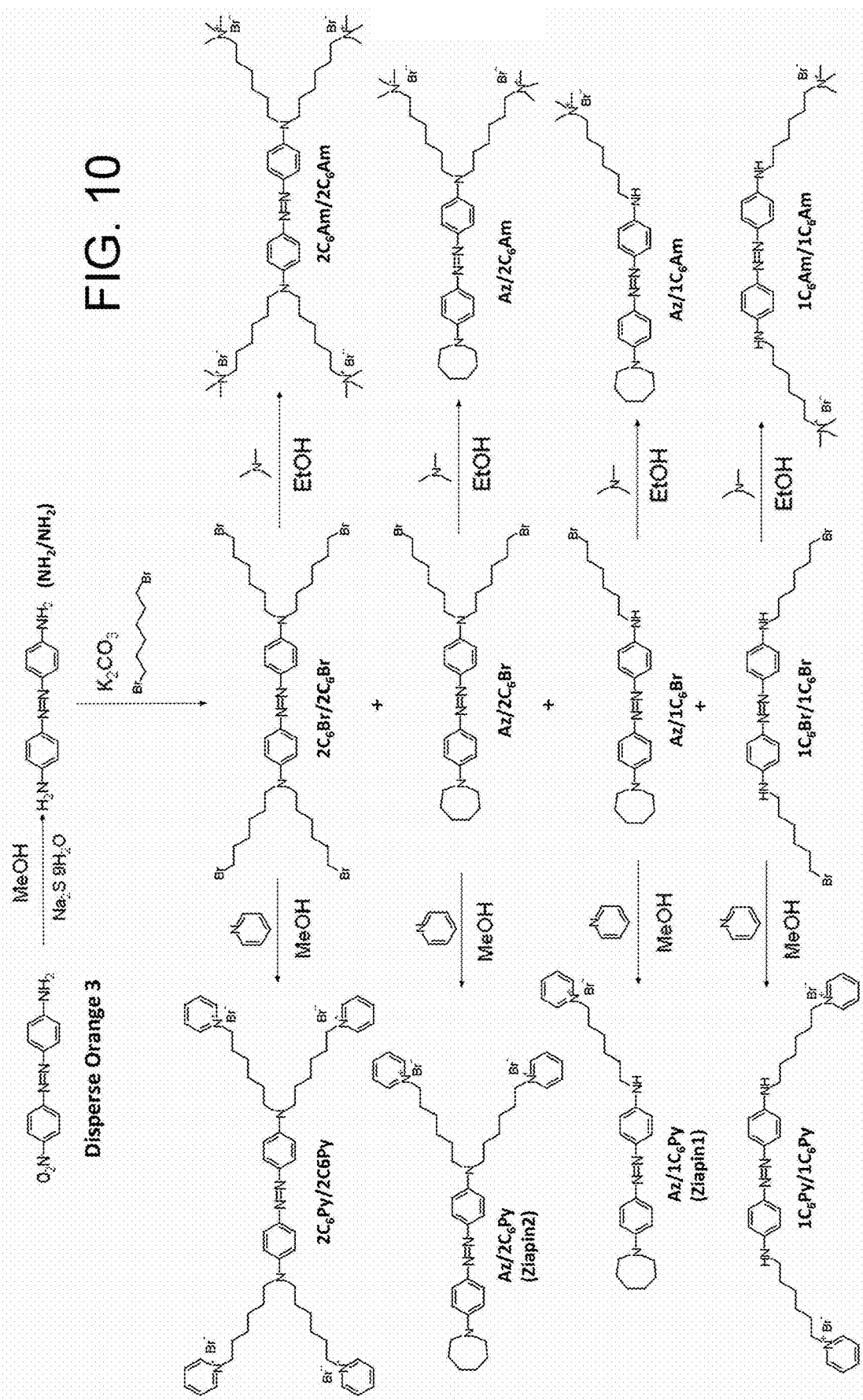
FIGS. 10 and 11: diagrams showing the preparation of preferred compounds according to the invention.
Figure 11:
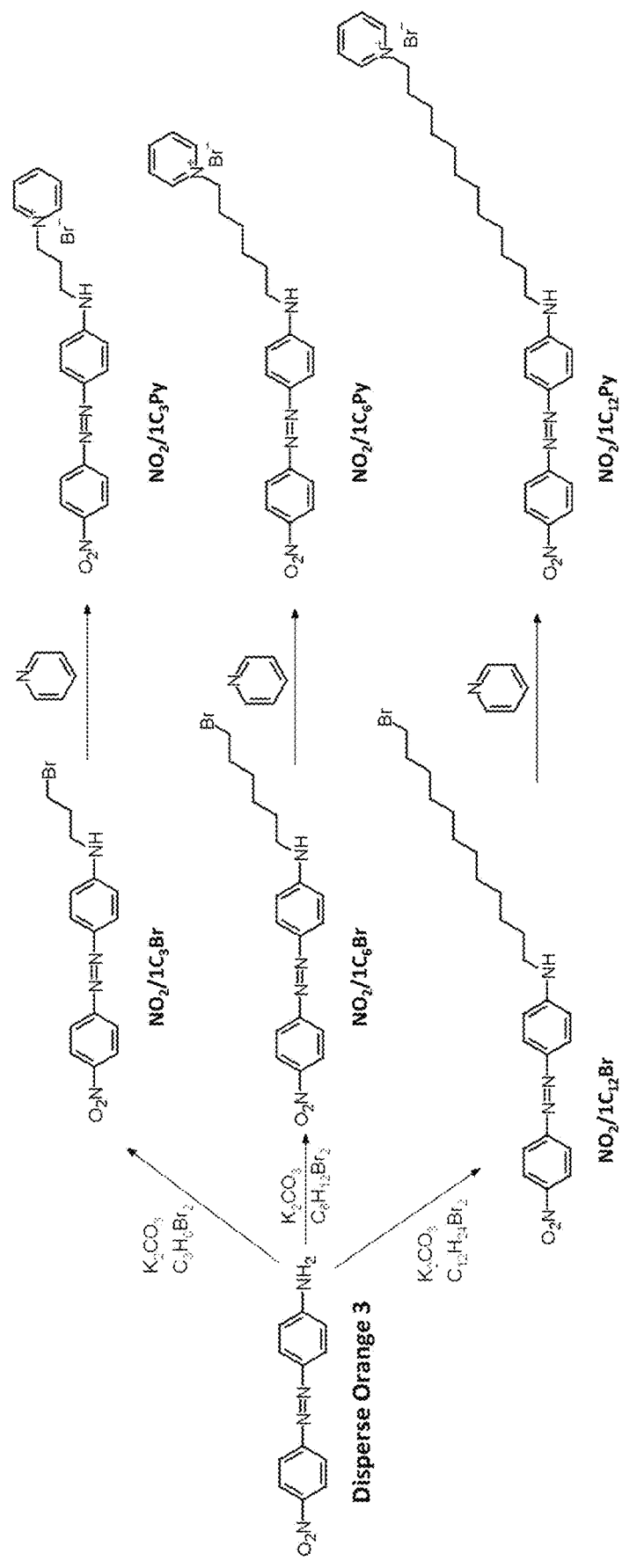
Figure 12:
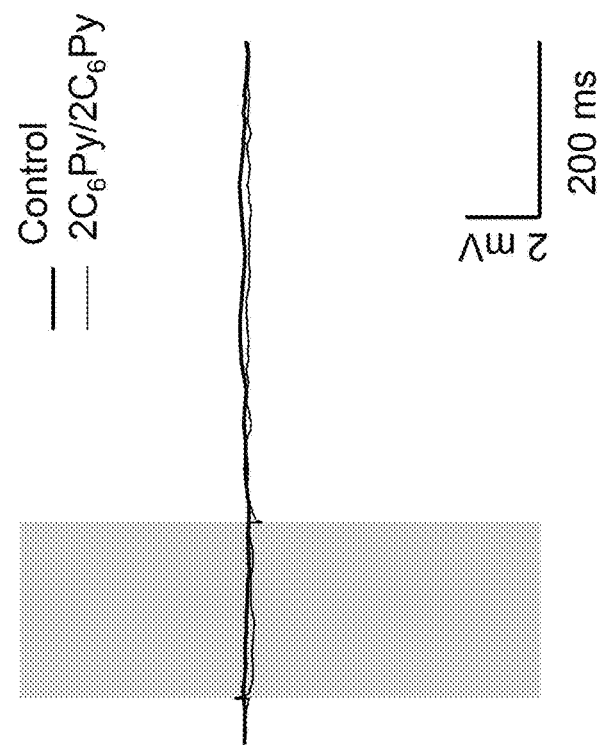
FIGS. 12 to 17: results of electrophysiological tests conducted on $HEK_{293}$ cells for some of the compounds according to the invention.
Figure 12:
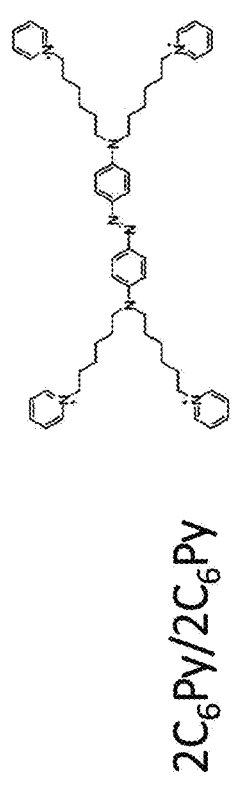
Figure 12:
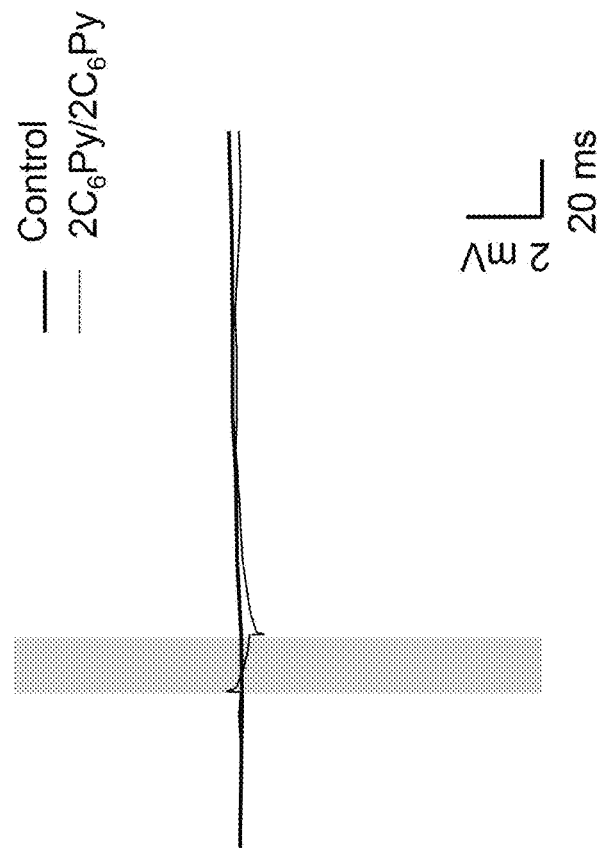
Figure 13:
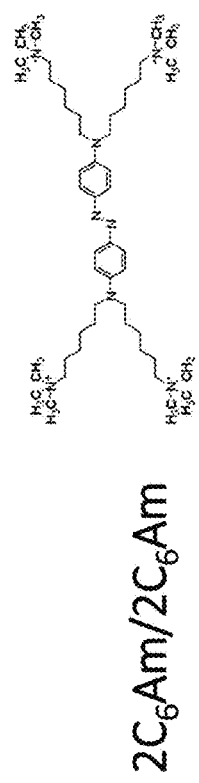
Figure 13:
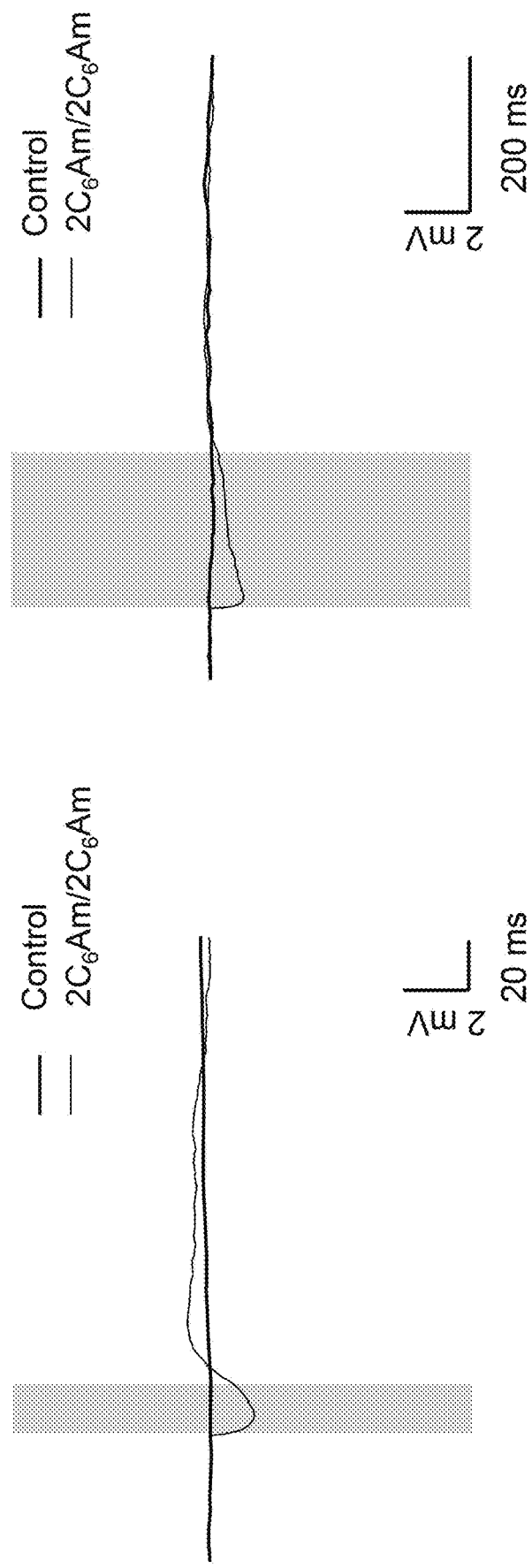
Figure 14:
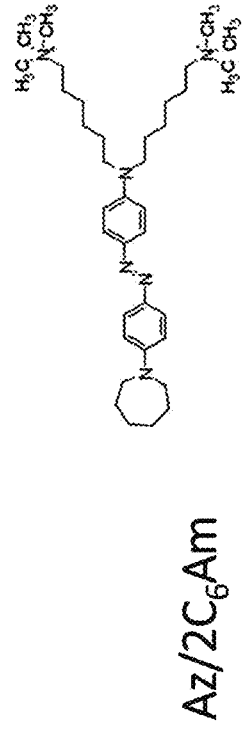
Figure 14:
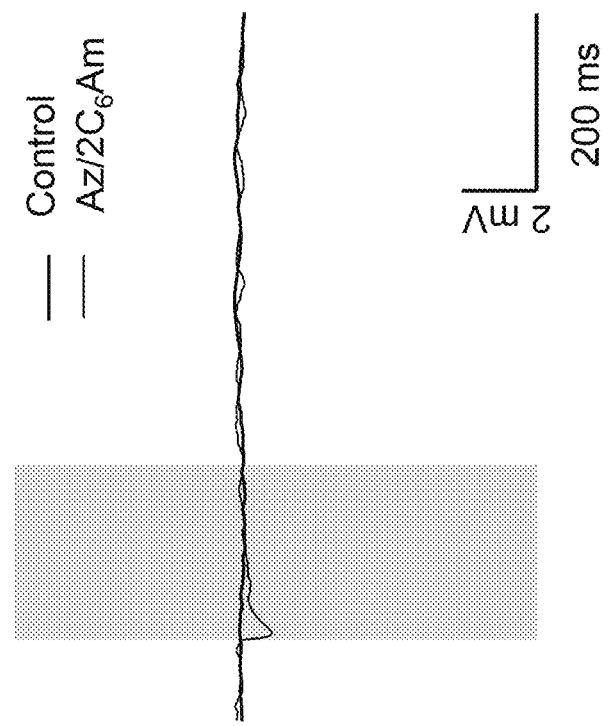
Figure 14:
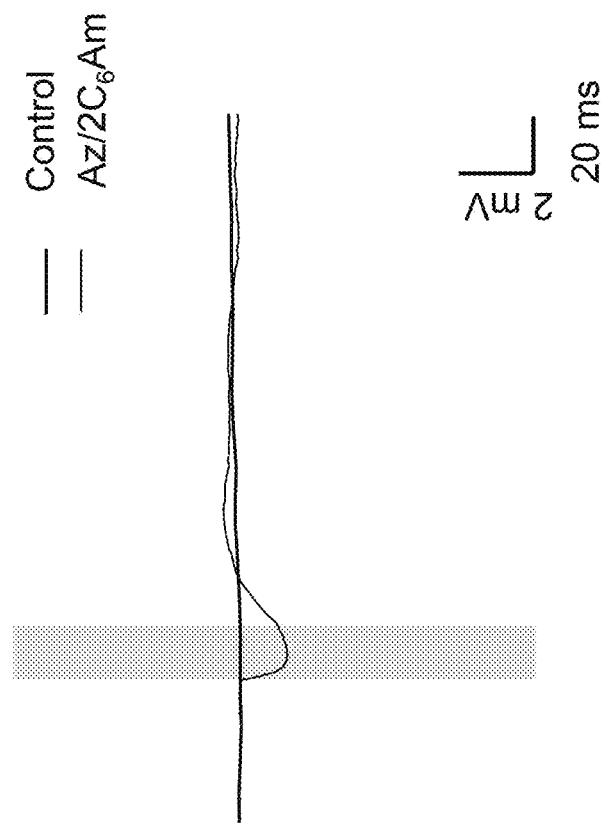
Figure 15:
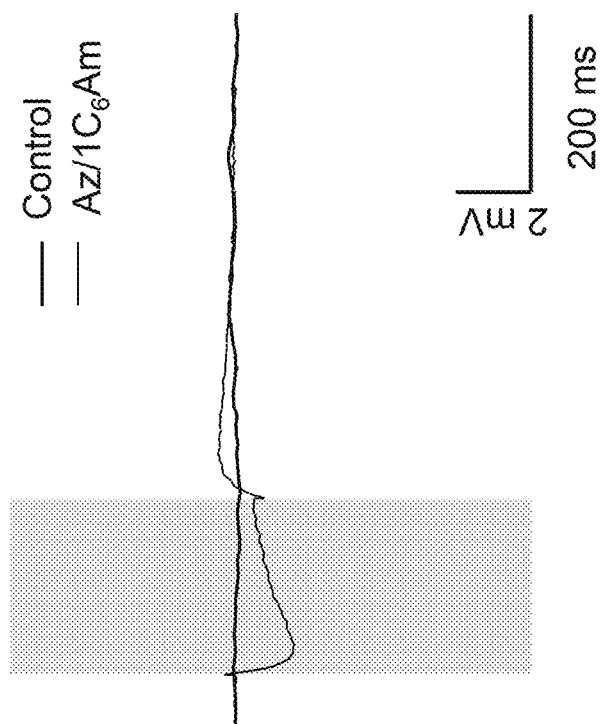
Figure 15:
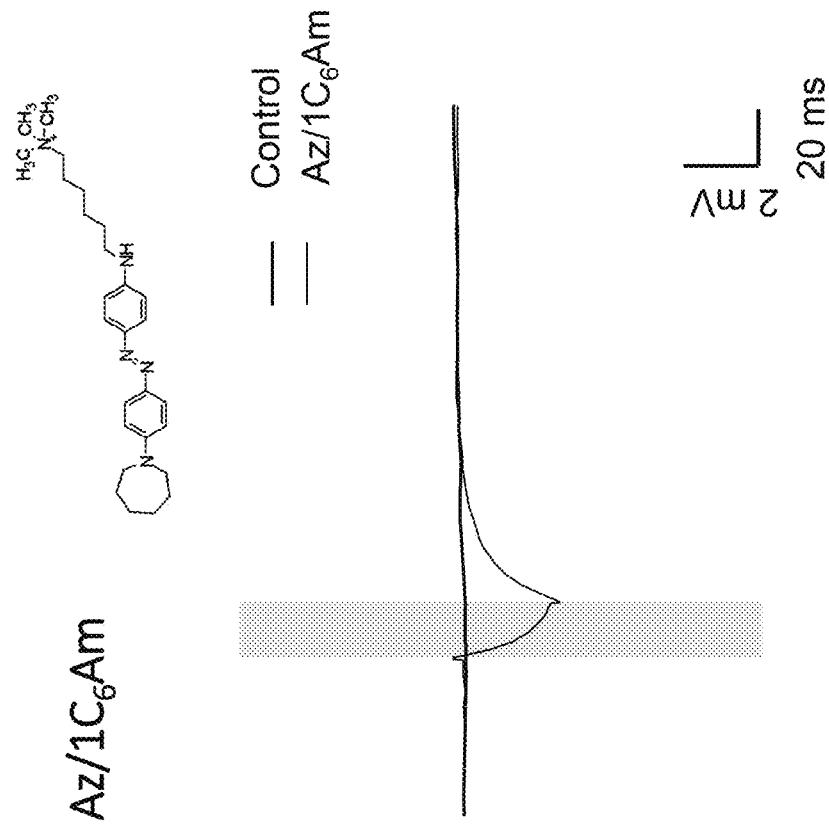
Figure 16:
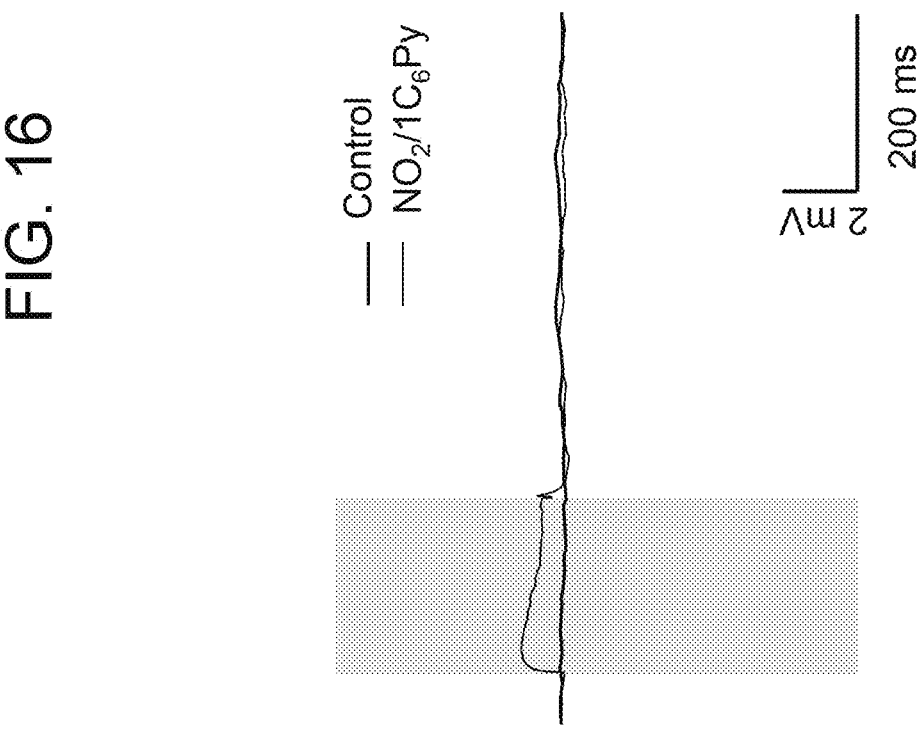
Figure 16:
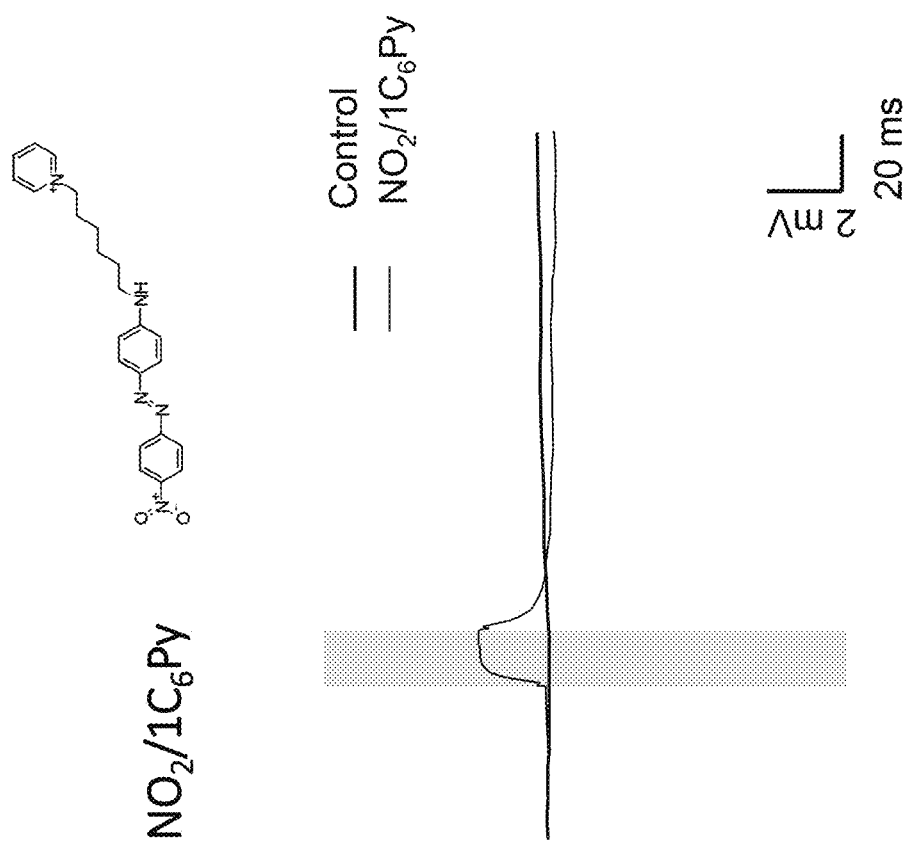
Figure 17:
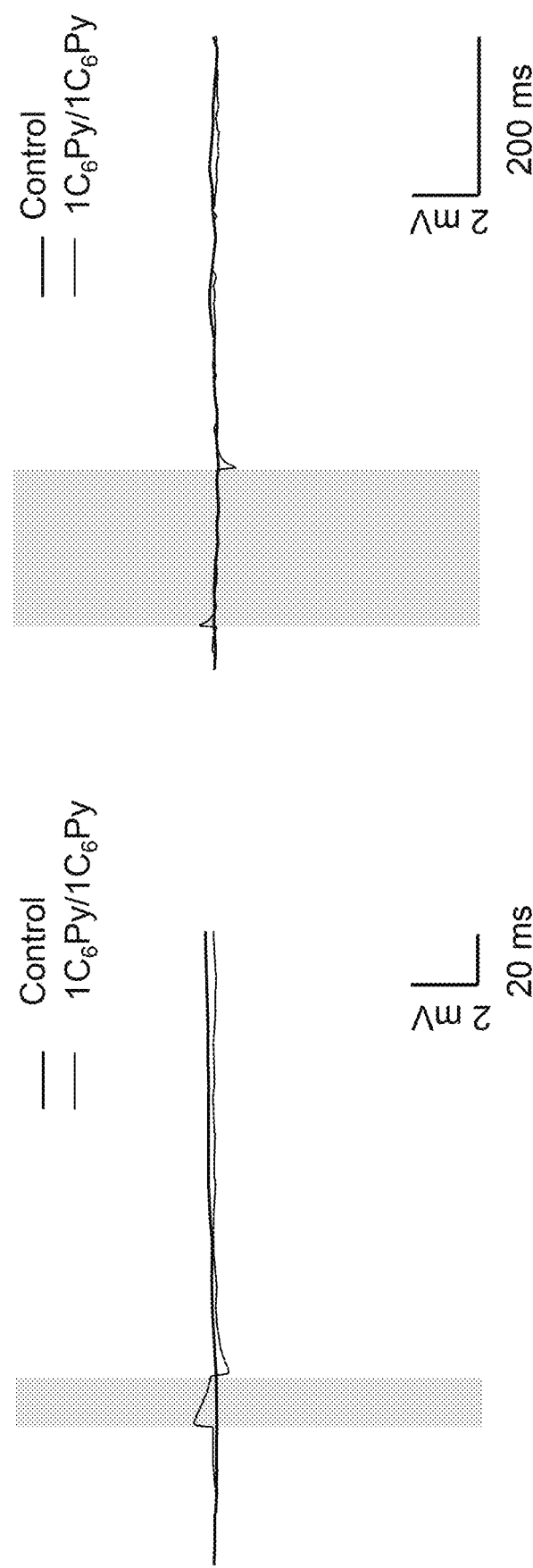

The synthetic route of two of the compounds according to the present invention, illustrated also in FIGS. 10 and 11, is described below. The person skilled in the art knows how to modify the synthetic strategy given herein to obtain the further compounds described herein. Unless otherwise specified, all reagents and solvents are commercially available and used without further purification. Reactions of reagents and intermediates sensitive to air and water were carried out in dried glassware and under an argon atmosphere. If necessary, the solvents were anhydrified by the conventional method and stored under argon.

$2C_6Br/2C_6Br$, $Az/1C_6Br$, $Az/2C_6Br$ and $1C_6Br/1C_6Br$ 1.0 g of 4,4'-diaminoazobenzene ($NH_2/NH_2$), synthesized according to the procedure reported in L. Hamryszak et al (*J. Mol. Liq.*, 2012, 165, 12) was kept under stirring in 130 mL of anhydrous acetonitrile. 2.60 g of $K_2CO_3$ and 7.5 mL of 1,6-dibromohexane were added to the reaction mixture. The progress of the reaction was monitored by TLC for a total of 120 hours. The reaction mixture was filtered and the solid was washed three times with diethyl ether, ethyl acetate and dichloromethane. The dibromoexane excess was removed at reduced pressure ($3\times10^{-1}$ mbar) at 60° C. The raw material was purified by flash chromatography with silica gel using a mixture of hexane/diethyl ether 3:1 as a mobile phase to yield 52 mg of $2C_6Br/2C_6Br$, 32 mg of $Az/1C_6Br$, 33 mg of $Az/2C_6Br$ and 64 mg of $1C_6Br/1C_6Br$.

Ziapin1 ($Az/1C_6Py$)

12 mg of $Az/1C_6Br$ were dissolved in 3 mL of pyridine and kept under stirring at room temperature for 42 hours. Thereafter, 3 mL of methanol were added and subsequently stirred for 60 hours. The excess pyridine and methanol was removed from the reaction mixture at reduced pressure to yield a solid that was washed with small portions of hexane.

Ziapin2 ($Az/2C_6Py$)

12 mg of $Az/2C_6Br$ were dissolved in 3 mL of pyridine and kept under stirring at room temperature for 42 hours. Thereafter, 3 mL of methanol were added and subsequently stirred for 60 hours. The excess pyridine and methanol was removed from the reaction mixture at reduced pressure to yield a solid that was washed with small portions of hexane.

$2C_6Py/2C_6Py$ 12 mg of $2C_6Br/2C_6Br$ were dissolved in 3 mL of pyridine and kept under stirring at room temperature for 42 hours. Thereafter, 3 mL of methanol were added and subsequently stirred for 60 hours. The excess pyridine and methanol was removed from the reaction mixture at reduced pressure to yield a solid that was washed with small portions of hexane.

$1C_6Py/1C_6Py$ 12 mg of $1C_6Br/1C_6Br$ were dissolved in 3 mL of pyridine and kept under stirring at room temperature for 42 hours. Thereafter, 3 mL of methanol were added and subsequently stirred for 60 hours. The excess pyridine and methanol was removed from the reaction mixture at reduced pressure to yield a solid that was washed with small portions of hexane.

$1C_6Am/1C_6Am$ 32 mg of $1C_6Br/1C_6Br$ were dissolved in 4 mL of ethanol and 0.3 mL of trimethylamine were added. The solution was heated to 80° C. for 48 hours. The excess of trimethylamine and ethanol was removed from the reaction mixture at reduced pressure.

$Az/1C_6Am$ 32 mg of $Az/1C_6Br$ were dissolved in 4 mL of ethanol and 0.3 mL of trimethylamine were added. The solution was heated to 80° C. for 48 hours. The excess of trimethylamine and ethanol was removed from the reaction mixture at reduced pressure.

$2C_6Am/2C_6Am$ 32 mg of $2C_6Br/2C_6Br$ were dissolved in 4 mL of ethanol and 0.3 mL of trimethylamine were added. The solution was heated to 80° C. for 48 hours. The excess of trimethylamine and ethanol was removed from the reaction mixture at reduced pressure.

$Az/2C_6Am$ 32 mg of $A/2C_6Br$ were dissolved in 4 mL of ethanol and 0.3 mL of trimethylamine were added in small portions. The solution was heated to 80° C. for 48 hours. The excess of trimethylamine and ethanol was removed from the reaction mixture at reduced pressure.

$NO_{2/1}C_3Br$ 1.0 g of Disperse Orange 3 was dissolved in 10 mL of anhydrous acetonitrile to which 1.0 g of $K_2CO_3$ and 1.7 mL of 1,3-dibromopropane were added. The reaction mixture was heated to 80° C. and the reaction was monitored by TLC for a total of 96 hours. The reaction mixture was then filtered and the solid was washed three times with diethyl ether, ethyl acetate and dichloromethane. The excess of dibromopropane was removed at reduced pressure ($3\times10^{-1}$ mbar) at 60° C. The raw material was purified by flash chromatography with silica gel using dichloromethane as a mobile phase, to yield 30 mg of NO2/1C3Br.

$NO_{2/1}C_6Br$ 1.0 g of Disperse Orange 3 was dissolved in 10 mL of anhydrous acetonitrile to which 1.0 g of $K_2CO_3$ and 0.7 mL of 1,6-dibromohexane were added. The solution was heated to 80° C. and the reaction was monitored by TLC for a total of 96 hours. The reaction mixture was then filtered and the solid was washed three times with diethyl ether, ethyl acetate and dichloromethane. The dibromoexane excess was removed at reduced pressure ($3\times10^{-1}$ mbar) at 60° C. The raw material was purified by flash chromatography with silica gel using diclomethane as a mobile phase, to yield 32 mg of $NO_2/1C_6Br$.

$NO_2/1C_{12}Br$ 1.0 g of Disperse Orange 3 was dissolved in 10 mL of anhydrous acetonitrile to which 1.0 g of $K_2CO_3$ and 5.5 g of 1,12-dibromododecane were added. The solution was heated to 80° C. and the reaction was monitored by TLC for a total of 96 hours. The reaction mixture was then filtered and the solid was washed three times with diethyl ether, ethyl acetate and dichloromethane. The raw material was purified by flash chromatography with silica gel using dichloromethane as a mobile phase to yield 40 mg of $NO_2/1C_{12}Br$.

$NO_2/1C_3Py$ 12 mg of $NO_2/1C_3Br$ were dissolved in 3 mL of pyridine and kept under stirring at room temperature for 42 hours. Thereafter, 3 mL of methanol were added and subsequently stirred for 60 hours. The excess pyridine and methanol was removed from the reaction mixture at reduced pressure to yield a solid that was washed with small portions of hexane.

$NO_2/1C_6Py$ 12 mg of $NO_2/1C_6Br$ were dissolved in 3 mL of pyridine and kept under stirring at room temperature for 42 hours. Thereafter, 3 mL of methanol were added and subsequently stirred for 60 hours. The excess pyridine and methanol was removed from the reaction mixture at reduced pressure to yield a solid that was washed with small portions of hexane.

$NO_2/1C_{12}Py$ 12 mg of $NO_2/1C_{12}Br$ were dissolved in 3 mL of pyridine and kept under stirring at room temperature for 42 hours. Thereafter, 3 mL of methanol were added and subsequently stirred for 60 hours. The excess pyridine and methanol was removed from the reaction mixture at reduced pressure to yield a solid that was washed with small portions of hexane.

Thin layer chromatography (TLC) was performed using silica gel on aluminum foil (Sigma Aldrich). The NMR spectra were obtained with a Bruker ARX400 instrument. Mass spectrometry was performed with a Bruker Equire 3000 plus instrument.

Photophysical Characterization

The Ziapin 2 molecule (FIG. 1a) in DMSO has a strong absorption peak centered at 470 nm (FIG. 1b) and a peak at 330nm, attributed respectively to the transitions n→Π* and Π→Π* of the E isomer. The irradiation with blue light (450 nm) leads to the isomerization E→Z, as can be seen from the weakening of the absorption of the E isomer accompanied by the concurrent increase in the absorption of the Z conformer at 350-380 nm and 520-60 nm. Azobenzene fluorescence is also an ideal tool for monitoring the switch behavior of photoreponsive materials, as well as the localization and photodynamics in living cells. The decrease of Ziapin 2 time-dependent fluorescence following exposure to blue light in DMSO solution (FIG. 1c) is related to the weakening of the photoluminescence of the E conformer due to the photoisomerization reaction. Time-dependent fluorescence measurements (FIG. 1d) indicate a clear "photo-switching" dynamics of azobenzene in living $HEK_{293}$ cells, with estimated isomerization/relaxation degrees of 0.01 $cm^2J^{-1}$ and $0.0085s^{-1}$. These values suggest that the photoswitching ability of Ziapin 2 in cell membranes is slightly less than that in DMSO, probably due to the restricted conformational freedom encountered by the molecule when internalized in the double layer structure. An analogous characterization was performed with the Ziapin 1 molecule (FIG. 1e,f).

Figure 18:
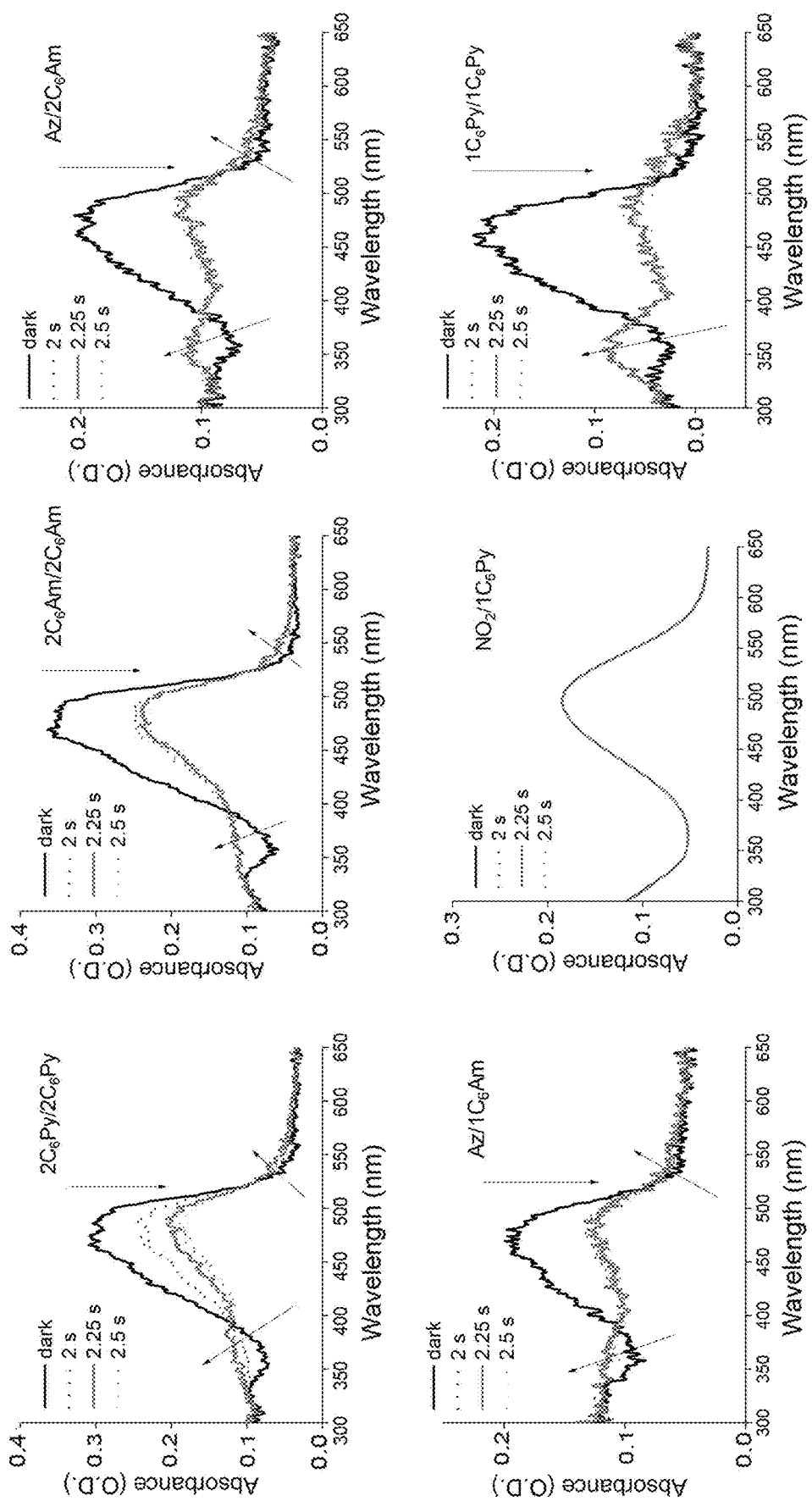
FIG. 18: UV-Vis absorption spectra of azobenzene derivatives at 470 nm, showing the trans-cis isomerization reaction of the compounds.

FIG. 18 shows the UV-Vis absorption spectra of the azobenzene derivatives at 470 nm, which show the trans-cis isomerization reaction of the compounds. The isomerization reaction for the compound $NO_2/1C_6Py$ is not observed, since in this case the nitro-azobenzene having a push-pull configuration has a rapid thermal relaxation (>ns) which hinders the appearance of the absorption of the cis isomer in the investigated temporal regime (Bandara et al., Chem. Soc. Rev., 2012, 41, 1809-1825).

Compound Localization Testing

Figure 2:
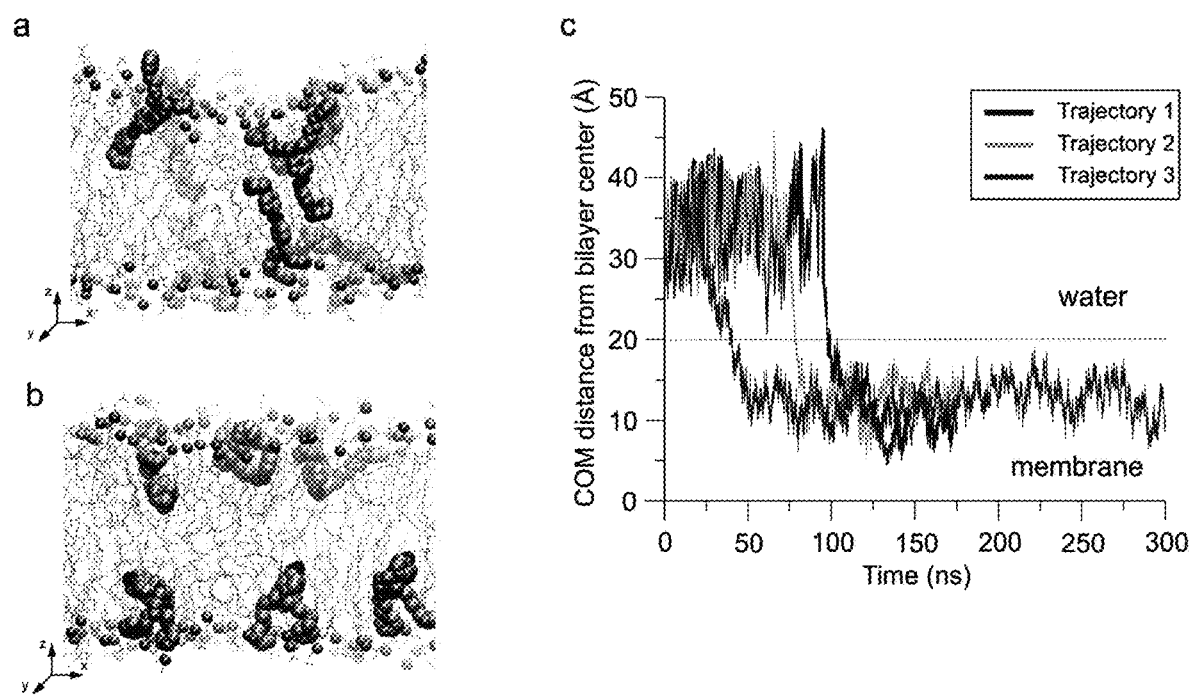
FIG. 2: molecular dynamics simulations of Ziapin 2 in the membrane model, (a) in E and (b) Z conformation. (c) temporal dependence of the distance between the center of mass (COM) of Ziapin 2 and the center of the double layer in three different simulations of a single Ziapin 2 (E) molecule in water and in the membrane environment (POPC lipid model); the dotted line roughly indicates the interface between water and the polar heads of the phospholipid groups.
Figure 3:
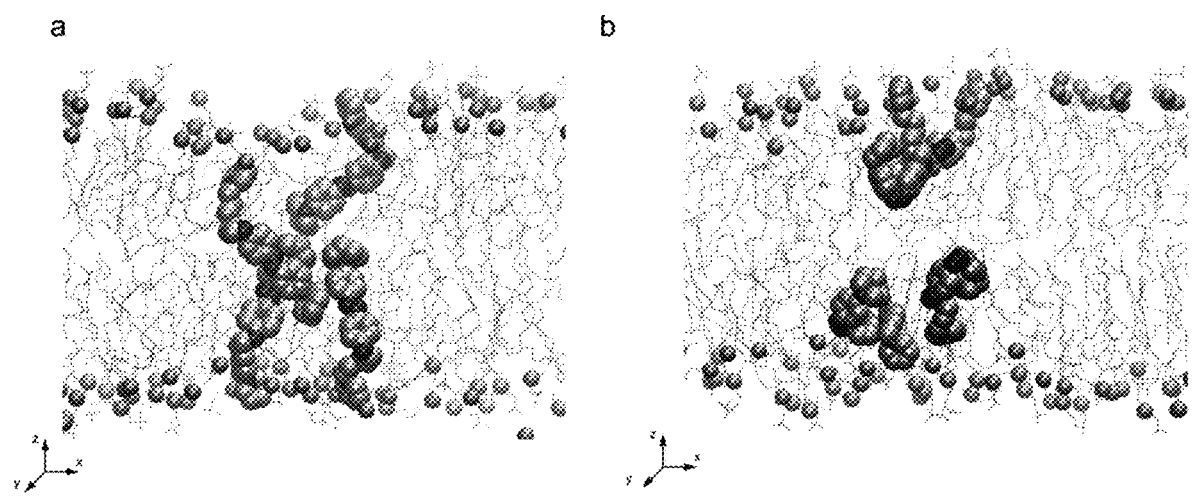
FIG. 3: molecular dynamics simulations of Ziapin 1 in the POPC membrane model, in E (a) and Z (b) conformation.
Figure 4:
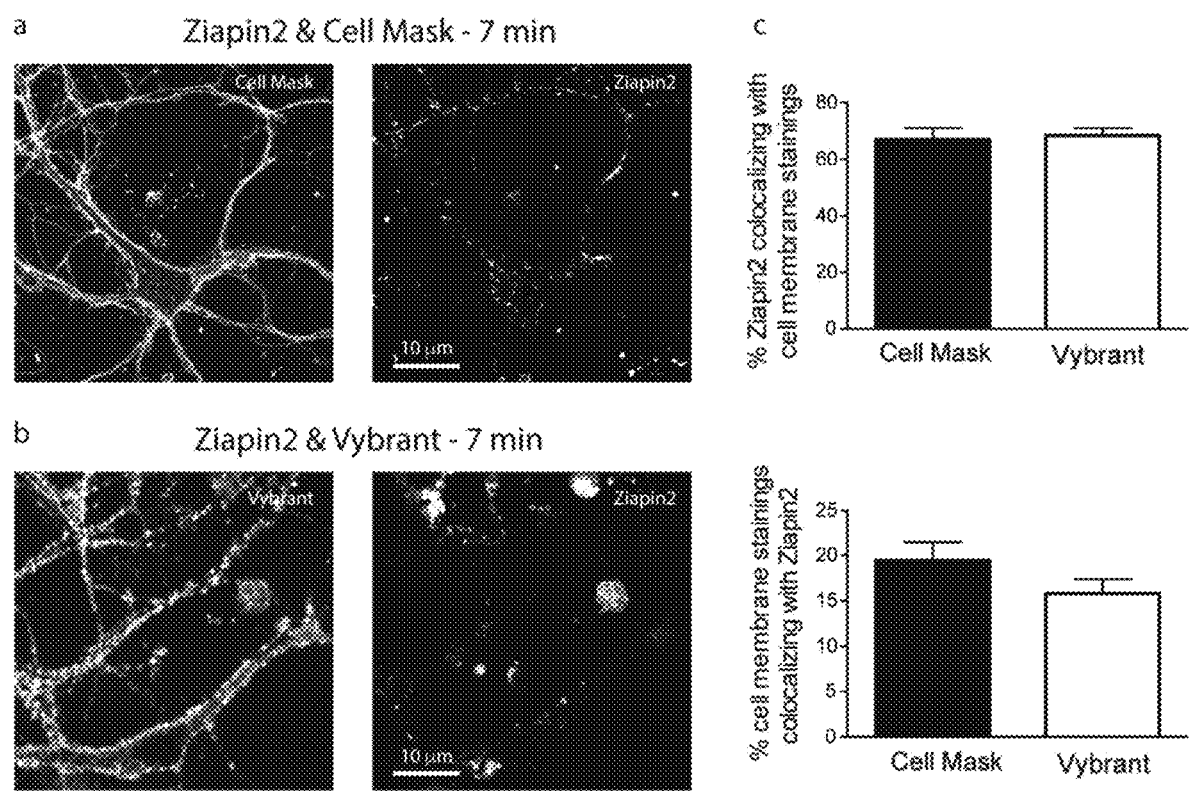
FIG. 4: confocal microscopy images showing the localization of the Ziapin 2 molecule in the vicinity of the plasma membranes (a) and in the lipid rafts (b) of primary neurons. Graph (c) shows that about 70% of Ziapin is located equally in plasma membranes and in lipid rafts (above) and that this leads to a coverage of about 20% of the cell surface (below).
Figure 5:
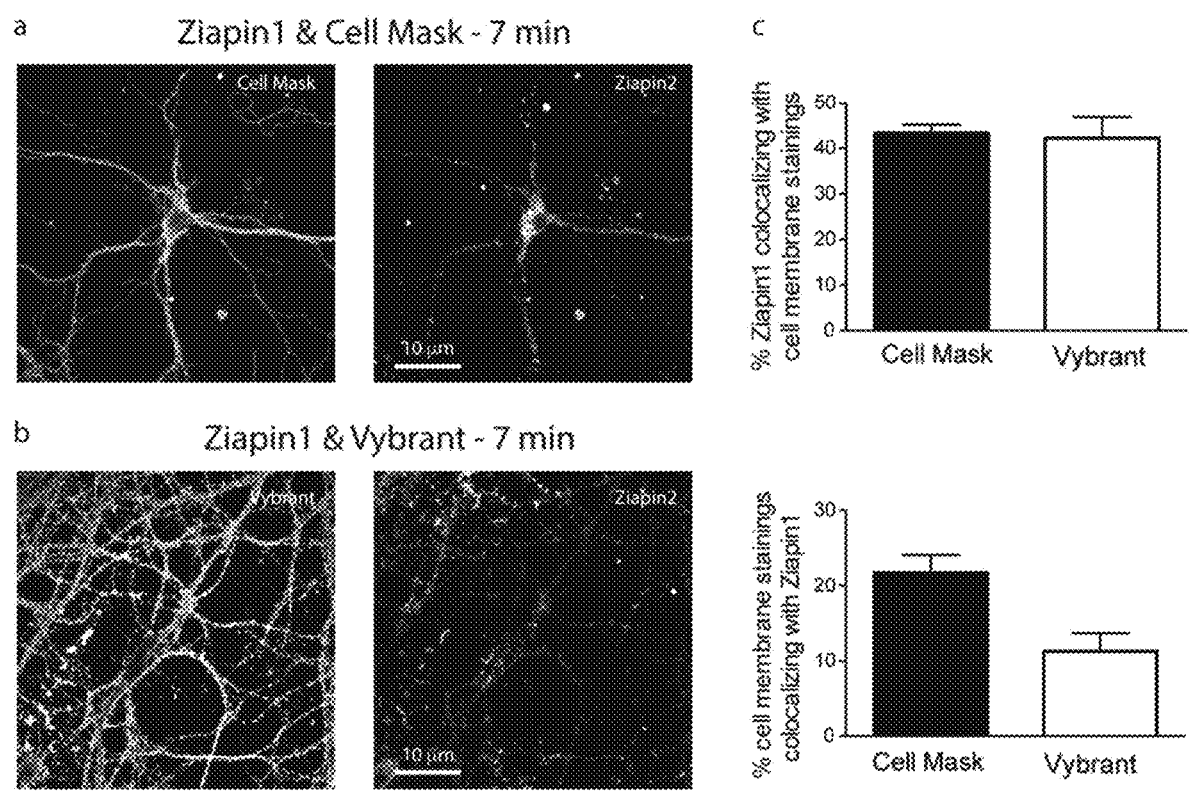
FIG. 5: confocal microscopy images showing the localization of the Ziapin 1 molecule in the vicinity of the plasma membranes (a) and in the lipid rafts (b) of primary neurons. Graph (c) shows that less than 50% of Ziapin 1 is located in plasma membranes and in lipid rafts (top), covering about 20% of the cell surface (bottom).

Molecules tend to localize in cell membranes and change their conformation. The specific affinity for the hydrophobic membrane environment was studied by molecular dynamics simulations of the E and Z isomers of the Ziapin 2 molecule (FIG. 2a) and revealed a significant tendency to incorporation into the membrane if the compound is added to the extracellular environment in a time variable between 50 and 100 ns (FIG. 2b). The Ziapin 1 molecule has also shown a tendency to insert into the membrane, showing however less deformation of the same (FIG. 3 a,b). The targeting of both molecules at the plasma membrane level was analyzed in cultures of primary neurons using specific markers for the cell membrane (Cell Mask, FIG. 4a, FIG. 5a, respectively) or for lipid rafts, membrane areas rich in cholesterol and ion channels (Vybrant, FIG. 4b, FIG. 5b, respectively). Following an exposure of the neuronal cultures to the compound, the percentage of localization of the molecules at the lipid rafts is very high, suggesting a marked affinity for the membrane areas rich in cholesterol and ion channels (FIG. 4c). This effect is considerably more marked for the Ziapin 2 molecule than for Ziapin 1 (FIG. 5c).

Molecule Activity

Following the optical excitation with visible light, the E form isomerizes into the Z form with greater steric hindrance. Following this conformational variation, the $HEK_{293}$ cell line responds with a hyperpolarization of the membrane potential (FIG. 6a and b), interpreted as the consequence of the deformation of the duel lipid layer that can influence the capacity and resistance of the membrane.

Figure 6:
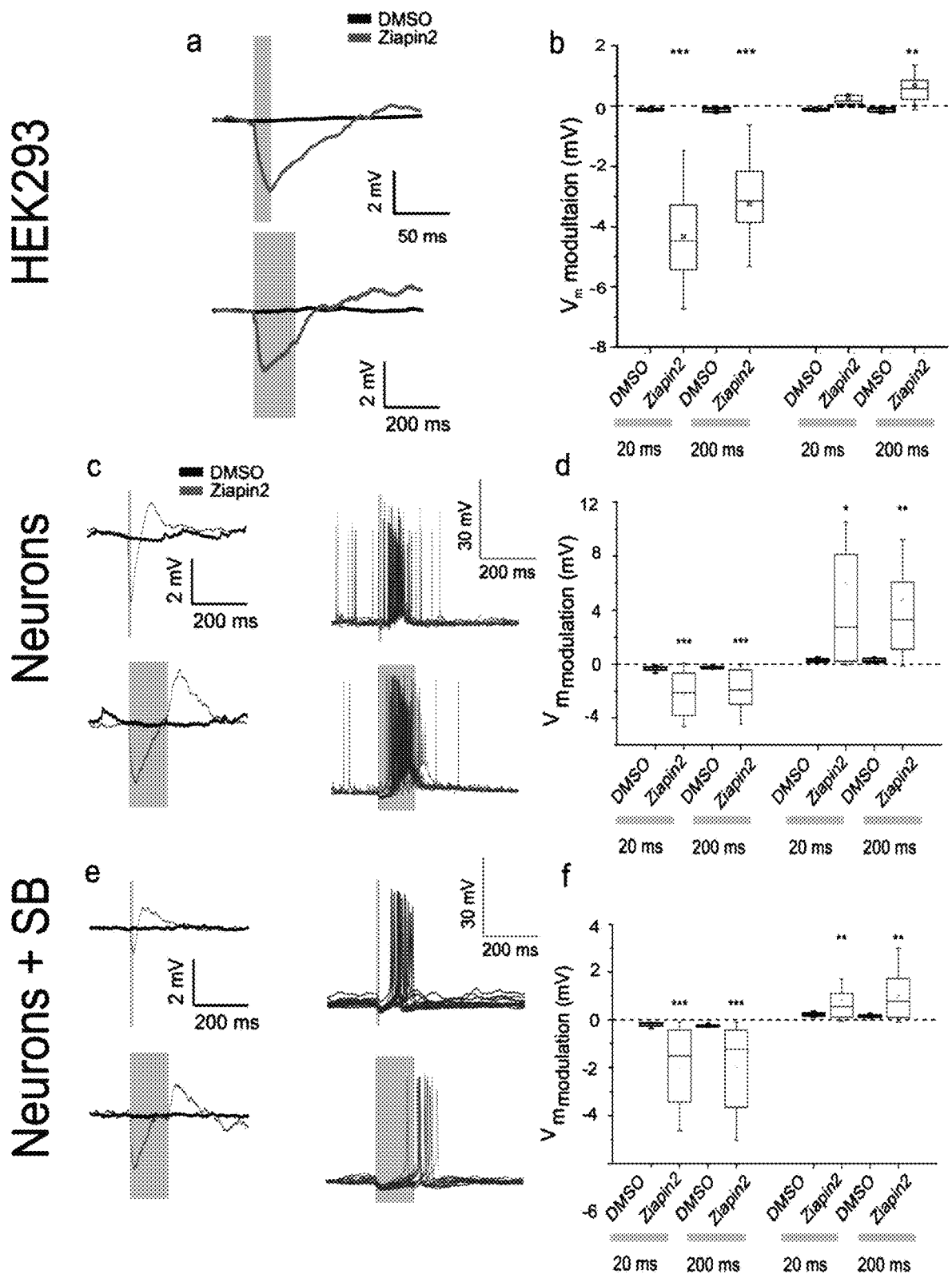
FIG. 6: electrophysiology conducted on $HEK_{293}$ cells (a, b), primary neurons in the absence (c, d) or in the presence of synaptic blockers (e, f) treated with Ziapin 2 and under illumination. (a) Representative average current-clamp traces recorded from $HEK_{293}$ cells incubated with DMSO 0.25% (v/v) (Ctrl; black line) or 25 µM Ziapin 2 in DMSO (gray line) and photostimulated for 20 ms (top) or 200 ms (bottom) (wavelength 470 nm, light power density of 47 mW/mm$^2$, shaded areas in gray). (b) Average hyperpolarization and subsequent depolarization in $HEK_{293}$ cells. (c, d) Representative current-clamp traces of passive (hyperpolarization/depolarization, left) and active (action potentials, right) responses recorded from neurons incubated in DMSO 0.25% (v/v) (Ctrl; black line) or with 5 µM Ziapin 2 in DMSO (gray line) in the absence (c) or presence (e) of synaptic blockers. The duration of light stimulation (20 and 200 ms, respectively) is indicated as a shaded area (wavelength 470 nm, light power density of 20 mW/mm$^2$). (d, f) Quantification of the hyperpolarization (left) and depolarization (right) peak in primary neurons exposed to DMSO or Ziapin 2 in the absence (d) or presence (f) of synaptic blockers and subjected to 20 or 200 ms of light stimulation.
Figure 7:
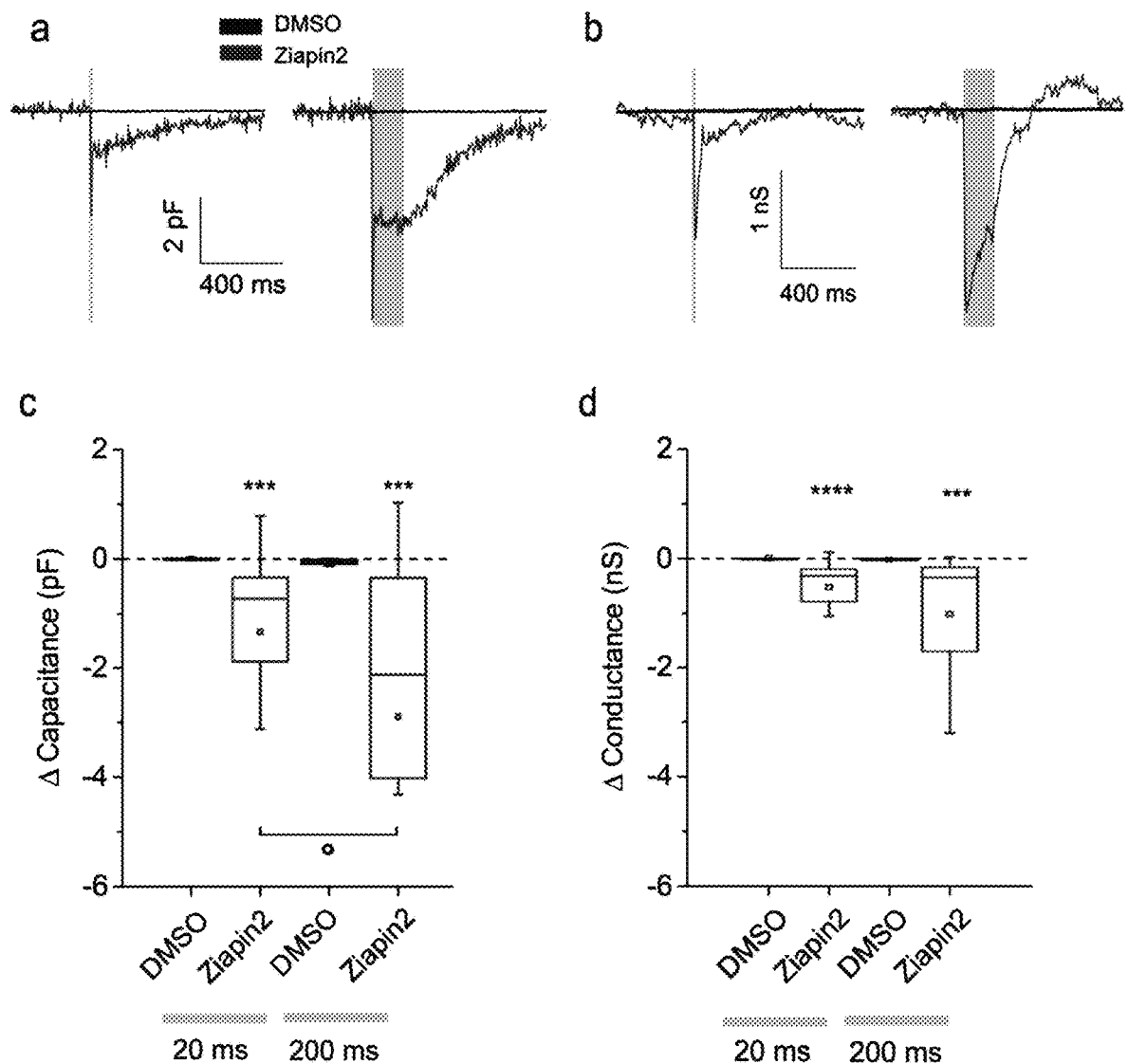
FIG. 7: modulation of membrane capacitance and conductance in primary neurons following light stimulation. Representative traces of capacity (a) and conductance (b) recorded in current-clamp from primary neurons incubated with 0.25% (v/v) DMSO (Ctrl; black line) or 5 µM Ziapin 2 in DMSO (gray line) in the presence of synaptic and photostimulated blockers with 20 ms (left) or 200 ms (right) (wavelength 470 nm, light power density of 20 mW/mm$^2$, shaded areas). (c, d) Quantification of peak capacity (c) and conductance (d) variations evoked by light stimuli of 20 and 200 ms.
Figure 8:
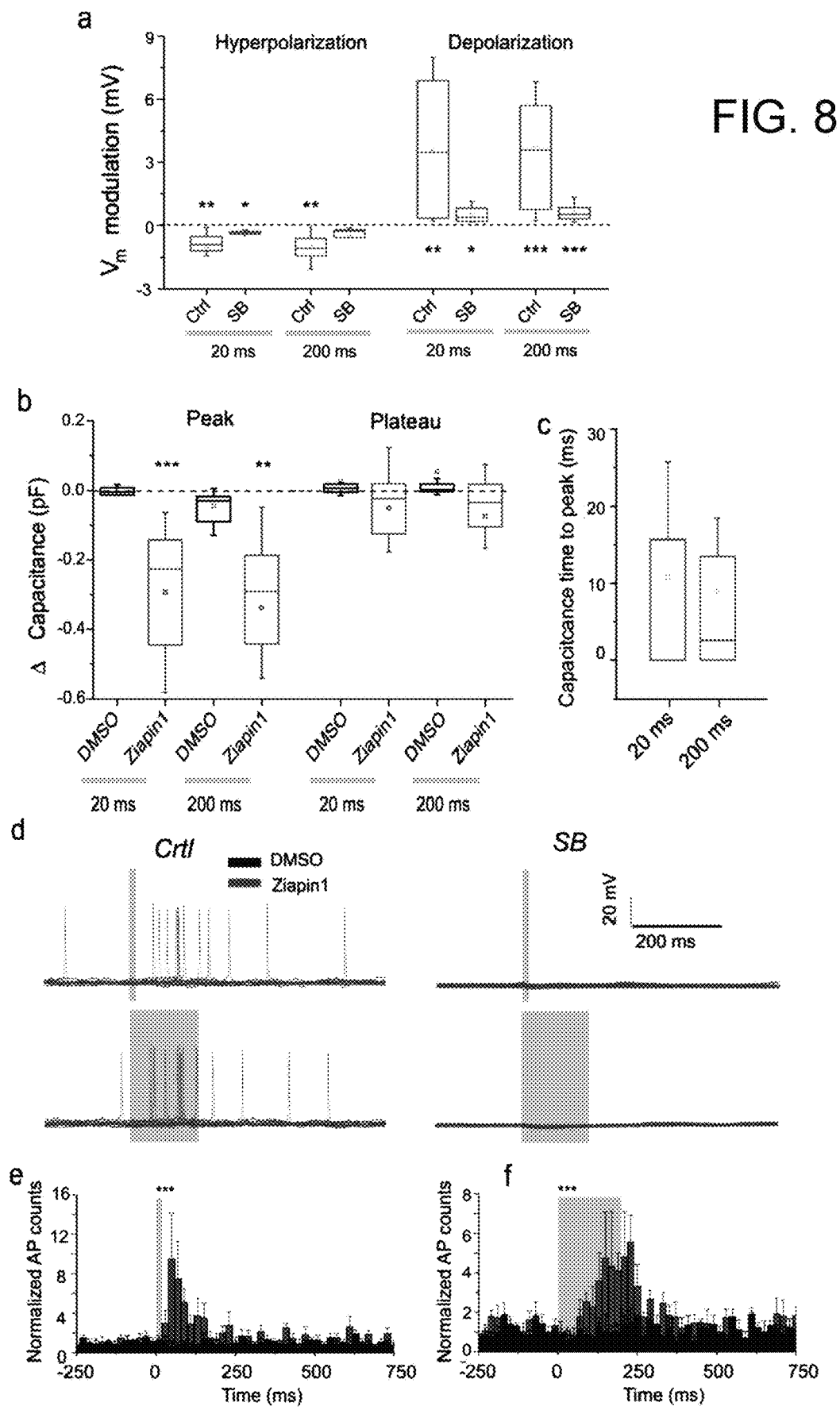
FIG. 8: effect of Ziapin 1 on passive and active membrane properties in primary hippocampal neurons. The primary neurons were incubated with DMSO (0.25% v/v) or Ziapin 1 (5 µM in DMSO) and subsequently recorded in the presence (SB) or absence (Ctrl) of synaptic blockers in response to light stimulation of 20 or 200 ms. (a) Quantification of hyperpolarization (left) and depolarization (right) in response to light stimulation for 20/200 ms. (b, c) Modulation of peak (left) and plateau (right) capacity (b) and of the temporal variation dynamics (c) evoked under light stimulation in neurons exposed to DMSO or Ziapin 1 in the presence of synaptic blockers. (d) Representative discharges of action potentials (firing) in primary neurons in DMSO (black line) or Ziapin 1 (gray line) in the absence (Ctrl) or presence of synaptic blockers (SB). (e, f) Quantification of the modulation of light-induced firing in neurons in DMSO (black) or Ziapin 1 (gray) recorded in response to light stimulation for 20 ms (e) or 200 ms (f).

In the case of excitable tissues provided with a large set of voltage-dependent conductances, such as primary neurons, hyperpolarization is followed by a depolarization that leads to reaching the threshold for action potential, with consequent firing in response to the light stimulus (FIG. 6c). The modulation of the membrane potential is not dependent on the duration of the light stimulus, while the amplitudes of hyperpolarization and subsequent depolarization are significantly different from the membrane potentials recorded in the presence of the vector alone (DMSO) (FIG. 6d). The biphasic effect on the membrane and firing potential of the compounds is also confirmed at the single neuron level in the presence of blockers of the inhibitory and excitatory synaptic activity (FIGS. 6e and f). The interaction of the compound with the membrane is also demonstrated by the modulation under light stimulation of the passive membrane properties (FIGS. 7a and b). In fact, both the capacity and the conductivity of the membrane show a significant decrease compared to the values in the dark (FIGS. 7c and d), corroborating the hypothesis of a modulation of neuronal activity linked to the deformation of the lipid bilayer. The passive and active membrane properties were also tested in primary neurons treated with the Ziapin 1 molecule, generally showing a lower modulation effect following light stimulation than that obtained with Ziapin 2 (FIG. 8).

Figure 9:
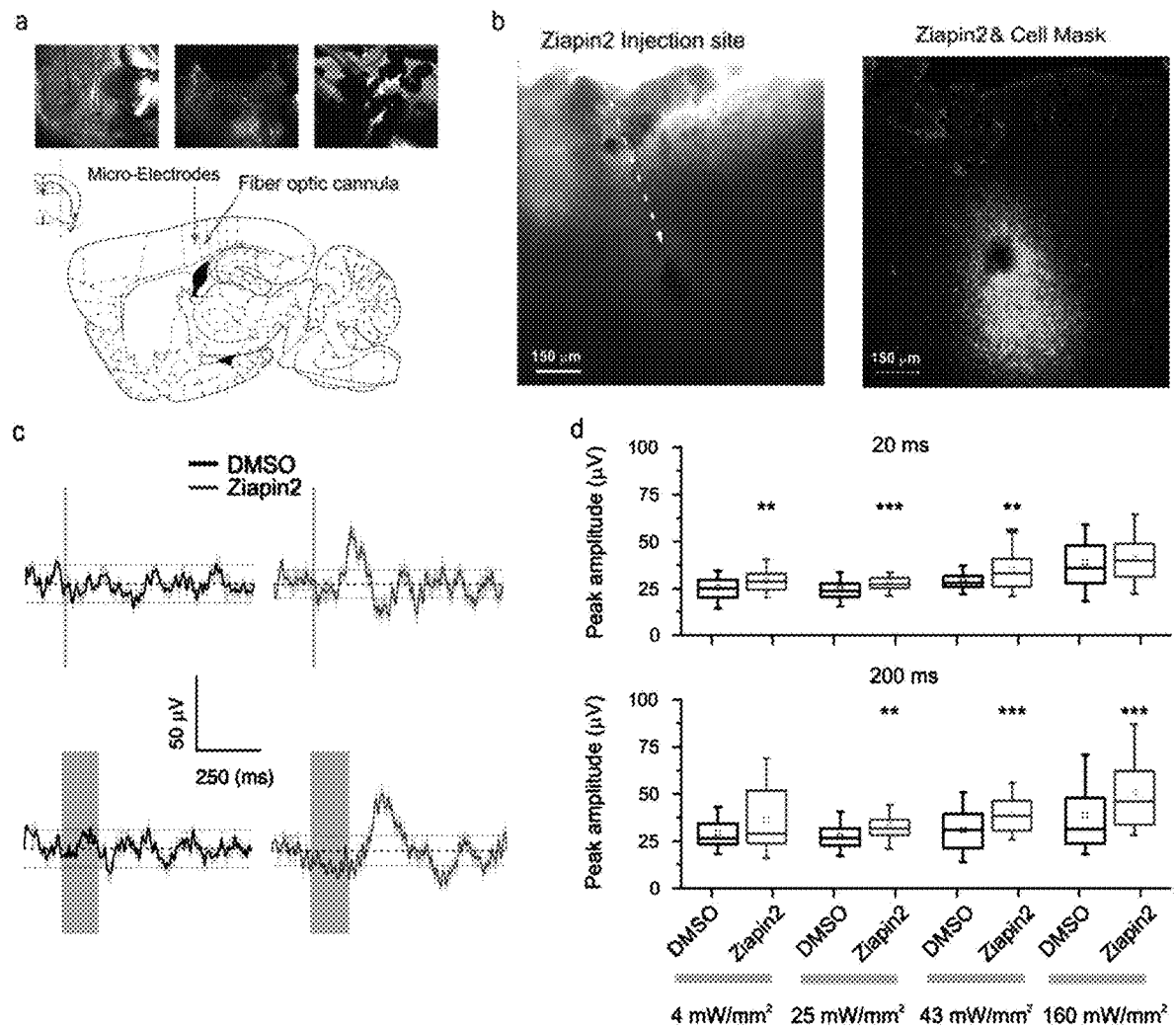
FIG. 9: cortical responses evoked by light in vivo in the somatosensory cortex of mice exposed to Ziapin 2. (a) Schematic representation of the stereotaxic injection of Ziapin 2 (200 mM in 1 µl of 10% DMSO) in the somatosensory cortex (S1ShNc, 2 mm anterior to lambda, 2 mm lateral to the midline and −723 µm ventral to the brain surface) and of the 16-fiber optic coupled microelectrode system for photostimulation and field potential recordings (LFP). (b) Representative LFP recordings evoked in the somatosensory cortex with light stimulation of 20 and 200 ms (43 mW/mm$^2$) in mice injected with DMSO (black line) or Ziapin 2 (gray line). The shaded areas represent light stimulation. (c) Dose-response analysis of LFPs in mice injected with DMSO (black line) or Ziapin 2 (gray line) depending on the power and duration of photostimulation. Stimulations at 25 and 43 mW/mm$^2$ trigger a response in animals injected with Ziapin 2, which is significantly different from animals treated with DMSO and 4 mW/mm$^2$ in the case of 20 ms illumination. Higher power densities elicit a response which, partially driven by temperature, is significantly higher in the presence of Ziapin 2. No significant changes were observed with respect to DMSO alone in the absence of the light stimulus and with the highest power used (160 mW/mm$^2$). *$p<0.05$; $p<0.01$; *$p<0.001$; Mann Whitney U-test (N=3 mice for both experimental groups).

The effectiveness of the compounds according to the present invention was demonstrated in vivo by the administration of 1 μl of Ziapin 2 in the somatosensory cortex of adult animals. The objective was to investigate whether the light-dependent modulation of neuronal activity observed in vitro occurred also in vivo. The electrophysiological recordings were obtained by implanting an array of 16 microelectrodes coupled to an optical fiber for photostimulation. Fluorescence analysis revealed that the area of diffusion and absorption of the molecule by cortical cells occupied a diameter of about 1 mm (FIGS. 9a and b). The optical stimulation for 20 and 200 ms with a 472 nm laser, at different intensities, induced a significant activation of the cortical activity evaluated in terms of field potentials (LFP). This result was not observed in animals treated with the carrier (DMSO). The response peaked at around 200 ms following the light stimulus (FIGS. 9c and d).

FIGS. 12 to 17 show the results of the electrophysiological tests conducted on HEK293 cells for some of the compounds according to the invention in the presence of 25 μM of compound when stimulated with short (20 ms, left) and long (200 ms, right) light pulses in the visible, represented by the shaded areas, to light having an intensity of 20 mW/mm$^2$. Each track is obtained as an average of 40 consecutive beams of light. In particular, in FIG. 16 it can be seen that the significant depolarization can be attributed to the charge transfer capacity of the derivative, which exhibits an electron acceptor-donor (push-pull) intramolecular configuration.

From the above description, the advantages offered by the compounds of the present patent application will be apparent to the person skilled in the art.

For example, it will be appreciated that the activity of the compounds described herein is not linked to the K$^+$ channels, therefore the use of the compounds according to the present invention is not associated with the risk of hyperexcitability linked to the block of K$^+$ channels, which inevitably accompanies the treatment with photochromic molecules of the prior art.

The invention claimed is:

1. A compound selected from the group comprising of:

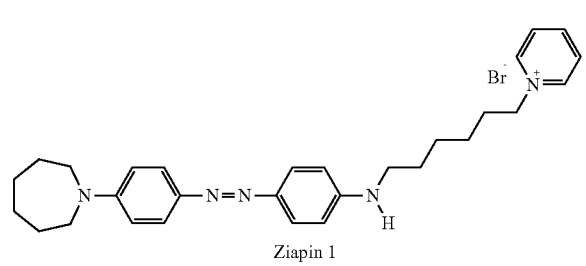

Ziapin 1

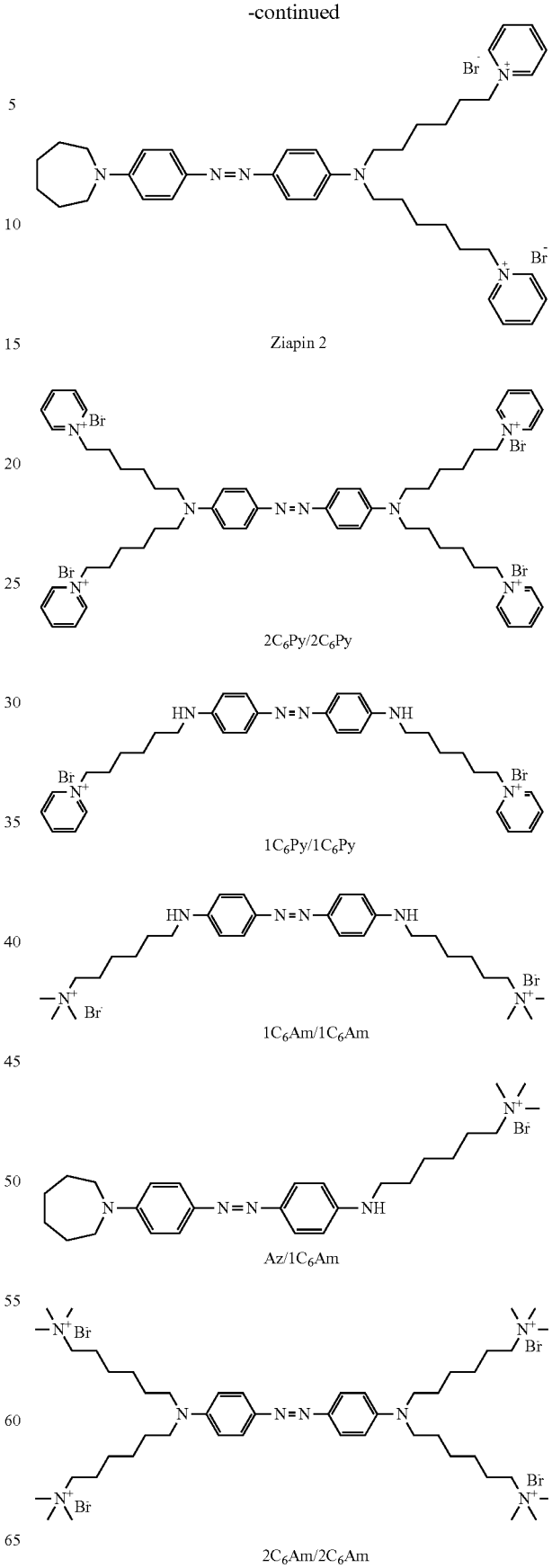

Ziapin 2

2C$_6$Py/2C$_6$Py

1C$_6$Py/1C$_6$Py

1C$_6$Am/1C$_6$Am

Az/1C$_6$Am

2C$_6$Am/2C$_6$Am

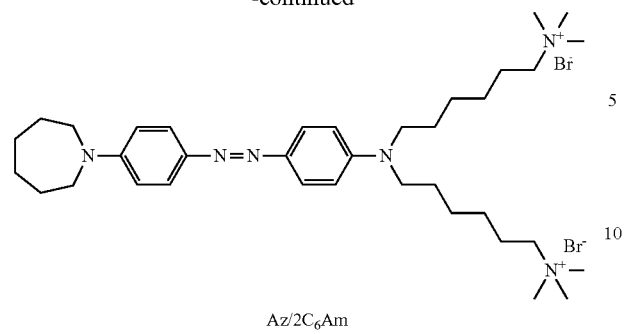
Az/2C₆Am
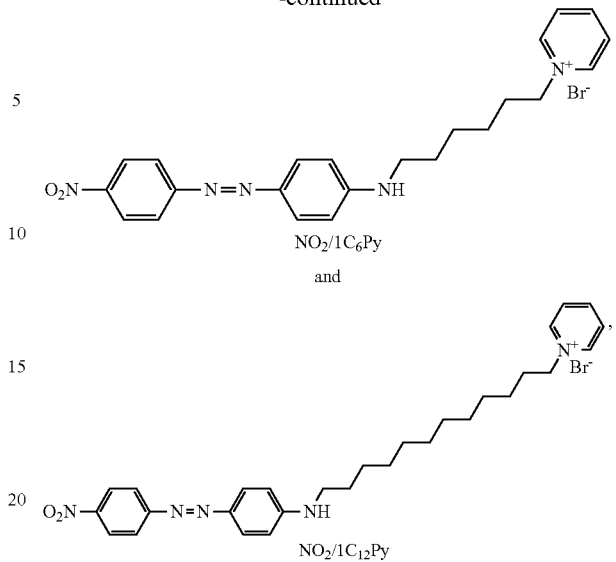
NO₂/1C₆Py
and
NO₂/1C₁₂Py
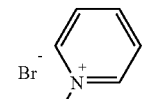
NO₂/1C₃Py
or any combinations thereof.
2. A method for the treatment of an eye disease, the method comprising administration of a suitable amount of a compound to a patient in need thereof, wherein the compound is selected from the group comprising of:
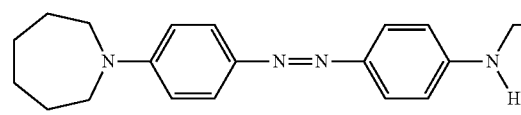
Ziapin 1
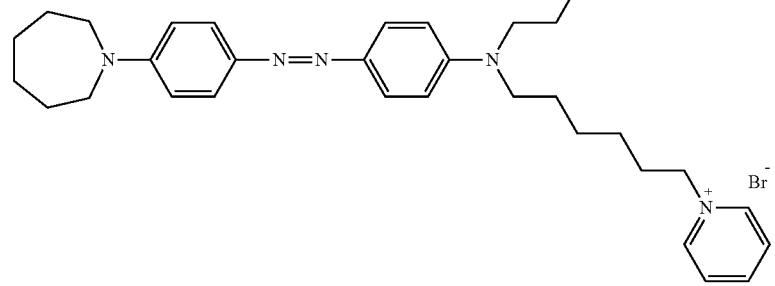
Ziapin 2

-continued
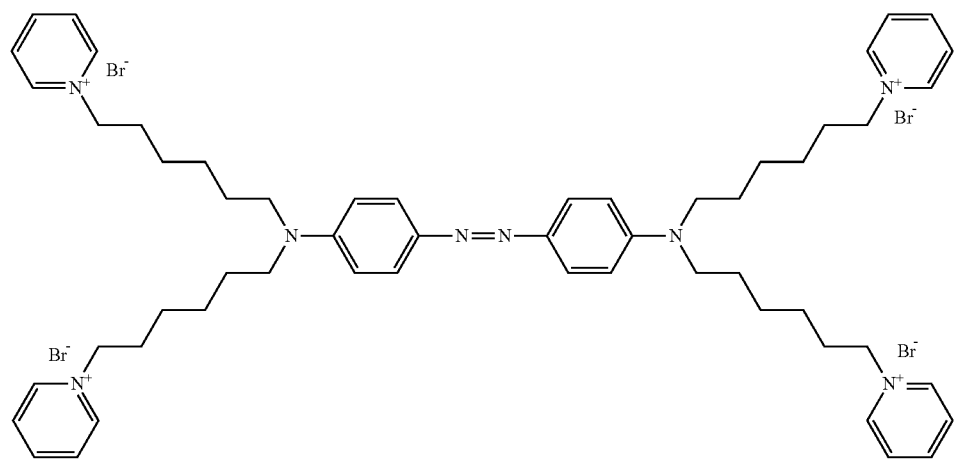
2C₆Py/2C6Py
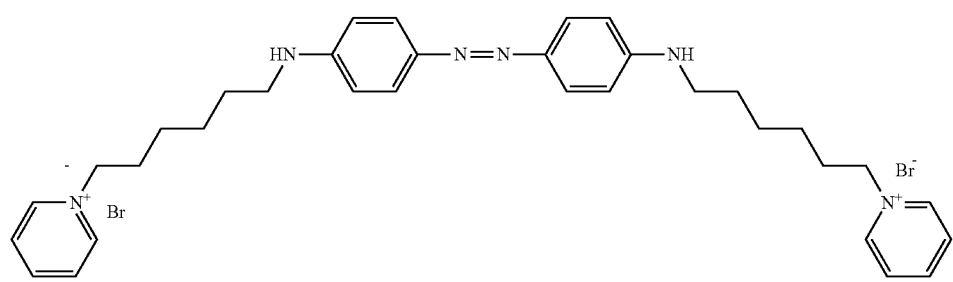
1C₆Py/1C₆Py
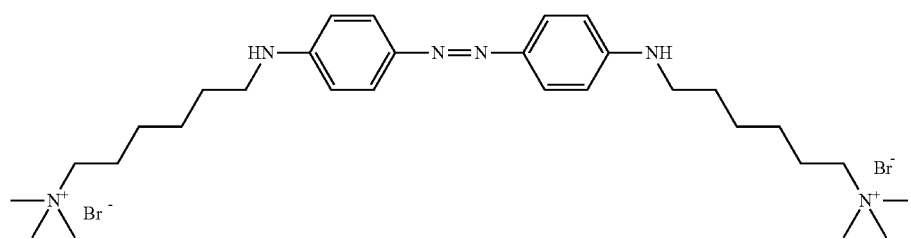
1C₆Am/1C₆Am
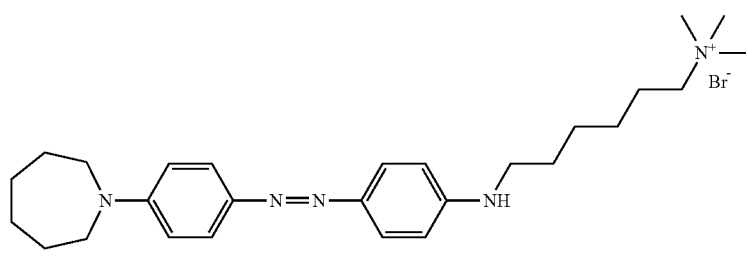
Az/1C₆Am -continued
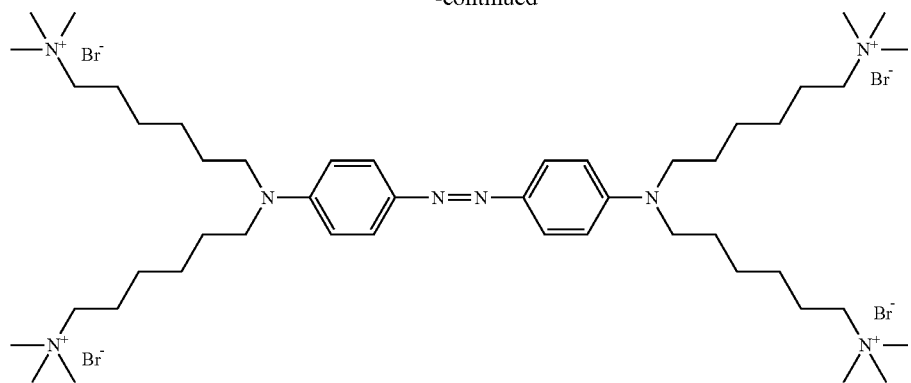
2C₆Am/2C₆Am
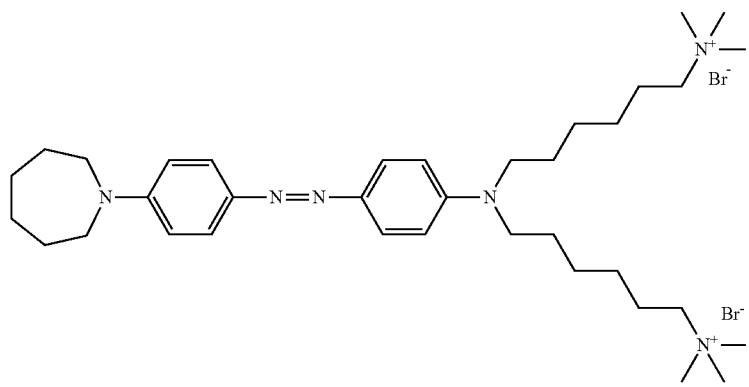
Az/2C₆Am
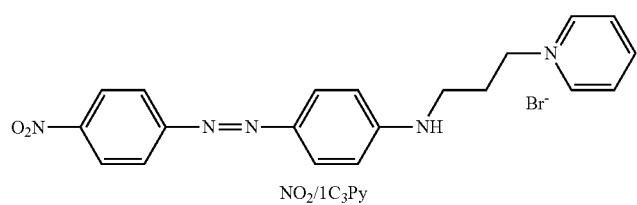
NO₂/1C₃Py
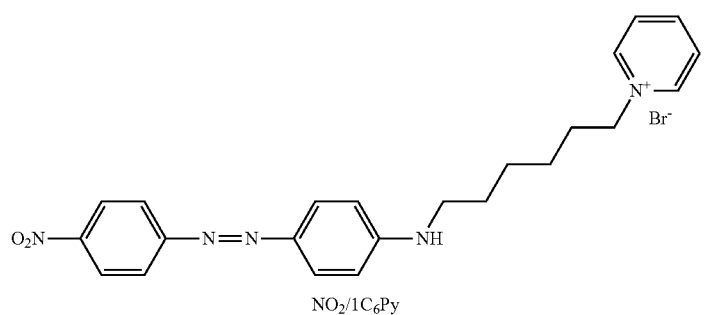
NO₂/1C₆Py -continued

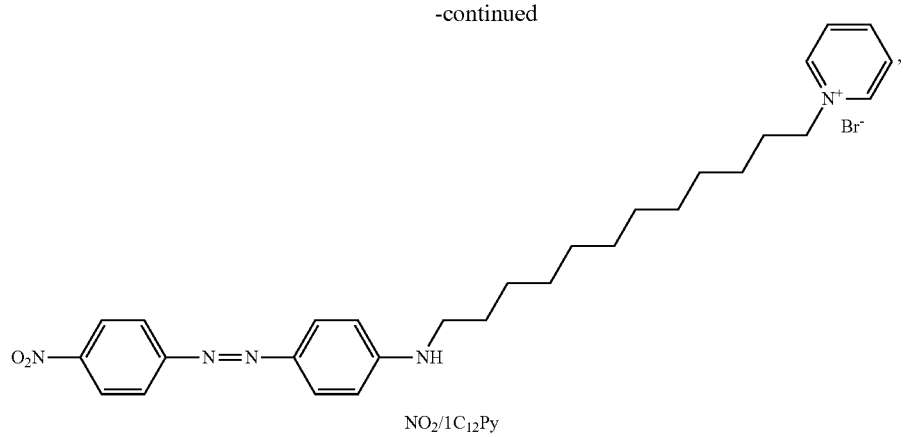

NO₂/1C₁₂Py or any combination thereof.

3. The method according to claim 2, wherein the eye disease is selected from the group comprising: retinitis pigmentosa, age-related macular degeneration, or combination thereof.

4. A composition comprising at least one of the compounds according to claim 1, and pharmaceutically acceptable excipients.

5. A composition according to claim 4, wherein the composition is formulated in the form of an intraocular injectable solution.

6. The composition according to claim 4, further comprising one or more active ingredients.

* * * * *